United States Patent [19]

Dingwall

[11] Patent Number: 4,895,588

[45] Date of Patent: Jan. 23, 1990

[54] SUBSTITUTED IMIDAZOLONES HAVING HERBICIDAL ACTIVITY

[75] Inventor: John G. Dingwall, Nuglar, Switzerland

[73] Assignee: Ciba-Geigy Corporation, Ardsley, N.Y.

[21] Appl. No.: 209,470

[22] Filed: Jun. 21, 1988

[30] Foreign Application Priority Data

Jul. 1, 1987 [CH] Switzerland .................. 2480/87

[51] Int. Cl.$^4$ .................... A01N 43/50; C07D 401/04
[52] U.S. Cl. ........................... 71/92; 546/112; 546/115; 546/167; 546/278
[58] Field of Search .................... 546/278; 71/92

[56] References Cited

U.S. PATENT DOCUMENTS

| | | | |
|---|---|---|---|
| 4,474,962 | 10/1984 | Wepplo | 546/167 |
| 4,608,079 | 8/1986 | Los | 71/92 |
| 4,693,741 | 9/1987 | Meyer et al. | 71/92 |
| 4,702,763 | 10/1987 | Maravetz | 71/90 |
| 4,709,036 | 11/1987 | Los et al. | 546/167 |
| 4,744,815 | 5/1988 | Baba et al. | 71/92 |
| 4,749,404 | 6/1988 | Parsons | 71/92 |
| 4,776,876 | 10/1988 | Nordhoff et al. | 71/92 |

FOREIGN PATENT DOCUMENTS

| | | |
|---|---|---|
| 041623 | 12/1981 | European Pat. Off. . |
| 041624 | 12/1981 | European Pat. Off. . |
| 133309 | 2/1985 | European Pat. Off. . |
| 2700270 | 7/1978 | Fed. Rep. of Germany . |
| 3420271 | 12/1984 | Fed. Rep. of Germany . |
| 3345901 | 6/1985 | Fed. Rep. of Germany . |
| 3403730 | 8/1985 | Fed. Rep. of Germany . |
| 2081505 | 12/1971 | France . |
| 639957 | 12/1983 | Switzerland . |
| 2172886 | 10/1986 | United Kingdom . |

OTHER PUBLICATIONS

Chem. Abstracts vol. 103 (1985) 103; 22590q.
Chem. Abstracts vol. 103 (1985) 103; 22591r.
Chem. Abstracts vol. 105 (1986) 105; 208886n.
Chem. Abstracts vol 73 (1970); 3856b.
Chem. Abstracts vol. 66 (1967); 94675m.

Primary Examiner—Richard A. Schwartz
Attorney, Agent, or Firm—Kevin T. Mansfield; Edward McC. Roberts

[57] ABSTRACT

The invention relates to novel herbicidally active compounds of formula I

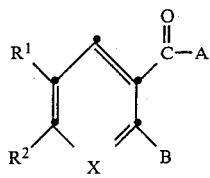

in which B represents an imidazolone of formula

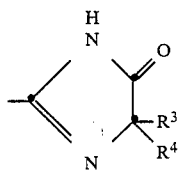

or A and B together represent a fused imidazolone of formula

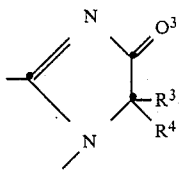

and the radicals X, $R^1$, $R^2$ and A in addition have the meanings given in the text and $R^3$ represents $C_1$–$C_4$-alkyl and $R^4$ represents a methyl or ethyl group substituted by from 1 to 5 fluorine atoms, processes for the preparation thereof, compositions containing compounds of formula I, methods of controlling weeds, and novel intermediates for the preparation of the compounds of formula I.

7 Claims, No Drawings

SUBSTITUTED IMIDAZOLONES HAVING HERBICIDAL ACTIVITY

The present invention relates to novel substituted imidazolones having herbicidal activity, to process for the preparation thereof, to compositions that contain those compounds, to novel intermediates for the preparation thereof, and to the use of the compounds according to the invention for controlling weeds and grasses.

The invention covers the novel compounds of formula I

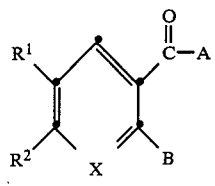

in which
X represents CH or N,
$R^1$ and $R^2$ independently of one another represent hydrogen; or $C_1$-$C_4$-alkyl optionally mono- or poly-substituted by halogen, nitro, cyano, $C_1$-$C_4$-alkoxy, $C_1$-$C_4$-haloalkoxy, $C_1$-$C_4$-alkylthio or by $C_1$-$C_4$-haloalkylthio; or $R^1$ and $R^2$, together with the carbon atoms of the six-membered ring to which they are bonded, form an unsaturated or partially unsaturated carbocyclic 5- or 6-membered ring or an unsaturated or partially unsaturated heterocyclic 5- or 6-membered ring containing up to two O or S atoms; and
A represents OH; $O^{\ominus}M^{\oplus}$; $C_1$-$C_4$-alkoxy; $C_3$-$C_5$-alkenyloxy;
$C_3$-$C_5$-alkynyloxy or $C_1$-$C_4$-alkoxy-$C_1$-$C_4$-alkoxy; and
$M^{\oplus}$ represents a cation equivalent of an alkali metal or alkaline earth metal or of a nitrogen-containing base; and
B represents an imidazolone of the formula

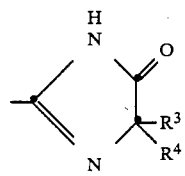

or
A and B together form a fused imidazolone of the formula

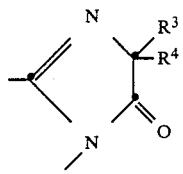

and
$R^3$ represents $C_1$-$C_4$-alkyl; and
$R^4$ represents a methyl or ethyl radical substituted by from 1 to 5 fluorine atoms,
and also salts of compounds of formula I with acids, bases and complex-formers.

The generic terms indicated as possible substituents for formula I include, for example, the specific individual substituents mentioned below; this list does not constitute any limitation of the subject of the invention.

Halogen is fluorine, chlorine, bromine and iodine, especially fluorine, chlorine and bromine, most especially, however, fluorine and chlorine.

$C_1$-$C_4$-alkyl includes methyl, ethyl, n-propyl, isopropyl, n-butyl, sec.-butyl, isobutyl and tert.-butyl.

The $C_3$-$C_5$-alkenyloxy and $C_3$-$C_5$-alkynyloxy radicals according to the invention are preferably bonded to the oxygen atom by way of a saturated carbon atom. The allyloxy and propargyloxy radicals should be given particular mention.

Haloalkyl is to be understood as meaning alkyl radicals in accordance with the scope of the particular definition that are wholly or partially substituted by the same or different halogen substituents. Preferred halogen substituents are fluorine and chlorine. Mention should be made of radicals such as, for example, 2,2,2-trifluoroethyl, 1,1,1,3,3,3-hexafluoroprop-2-yl, trifluoromethyl, difluoromethyl, trichloromethyl, dichloromethyl and difluoromethyl.

In the case of substituents that are composed of several basic elements, such as, for example, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkoxy-$C_1$-$C_4$-alkoxy, the partial elements in each case can be freely selected within the scope of their own definition.

In the present Application, the substituent $R^4$ represents a $C_1$-$C_2$-alkyl radical substituted by from 1 to 5 fluorine atoms, and it thus represents a radical selected from the group consisting of: $CF_3$, $CHF_2$, $CH_2F$, $CHFCH_3$, $CHFCH_2F$, $CHFCHF_2$, $CHFCF_3$, $CF_2CH_3$, $CF_2CH_2F$, $CF_2CHF_2$, $CF_2CF_3$, $CH_2CH_2F$, $CH_2CHF_2$ and $CH_2CF_3$.

In accordance with the definition, the radicals A and B in formula I can represent an imidazol-5-one radical that is fused by way of the 1 and 2 positions. In addition, B is defined as an imidazolone radical that is bonded by means of a single bond. Formula I thus covers the compounds of formulae Ia, Ib and Ic given below:

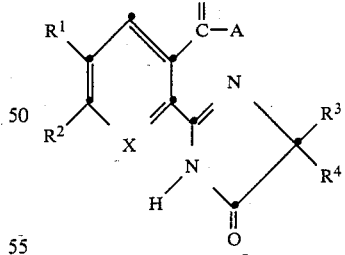
Ia

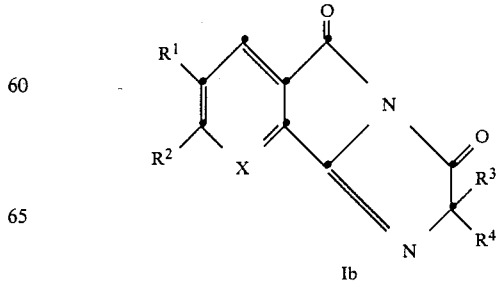
Ib

-continued

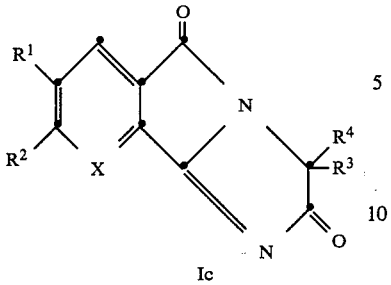

Furthermore, the radicals $R^1$ and $R^2$, together with the carbon atoms of the six-membered ring to which they are bonded, can form a fused unsaturated or partially unsaturated carbocyclic 5- or 6-membered ring. Depending on the meaning of X, the system on which formula I is based is then a naphthalene, dihydronaphthalene or tetrahydronaphthalene system, or an indan or dihydroindan system, whilst when $X=N$, the heterocycle on which formula I is based forms a quinoline, dihydroquinoline, tetrahydroquinoline, cyclopenta[b]pyridine or dihydrocyclopenta[b]pyridine system.

The pair of substituents $R^1/R^2$ can, however, also represent a fused heterocyclic 5- or 6-membered ring having up to 2 oxygen or sulphur atoms.

If X represents N, these fused partial rings, together with the pyridine ring, form, for example, a thiopheno[2,3-b]pyridine, thiopheno[3,2-b]-pyridine, dihydrothiopheno[2,3-b]pyridine, dihydrothiopheno[3,2-b]pyridine, dioxolo[4,5-b]pyridine, dihydropyrido[2,3-b]1,4-dioxine, pyrido[2,3d]1,3-dioxine, furo[2,3-b]pyridine, furo[3,2-b]pyridine, pyrano[3,4-b]pyridine, dihydropyrano[3,4-b]pyridine, pyrano[4,3-b]-pyridine or dihydropyrano[4,3-b]pyridine system, etc. If X represents CH, the fused substituent pair $R^1/R^2$, together with the six-membered ring, forms, for example, a benzo[b]furan, benzo[b]1,4-dioxine, benzo-[b]thiophene, dihydrobenzo[b]furan, dihydrobenzo[b]thiophene, dihydrobenzo[b]1,4-dioxine, dihydrobenzo[c]thiophene, dihydrobenzo[c]furan, chroman, isochroman, chromene or isochromene system, etc.

Suitable cations $M^\oplus$ are both the alkali metal and the alkaline earth metal ions of Li, Na, K, Rb, Mg or Ca, and also quaternary or protonated nitrogen-containing bases, such as $NH_4^\oplus$, $[N(H)_m(R)_n]^\oplus$ (where $m+n=4$ and $R=C_1-C_6$-alkyl optionally substituted by hydroxy, or $C_1-C_6$-alkoxy), or heterocyclic bases, such as morpholine or piperidine. Mention should be made, inter alia, of $NH(C_2H_5)_3^\oplus$ or $NH(CH_2CH_2OH)_3^\oplus$.

The compounds of formula I may be in various isomeric and tautomeric forms. Formula I also covers these isomers and tautomers, as well as the combinations of various stereoisomers.

The invention relates especially to compounds of formula I
in which
X represents CH or N,
$R^1$ and $R^2$ independently of one another represent hydrogen or $C_1-C_4$-alkyl; or
$R^1$ and $R^2$, together with the carbon atoms of the six-membered ring to which they are bonded, form an unsaturated or partially unsaturated carbocyclic 5- or 6-membered ring or an unsaturated or partially unsaturated heterocyclic 5- or 6-membered ring containing one O or S atom; and A represents OH; $O^\ominus M^\oplus$; $C_1-C_4$-alkoxy; $C_3-C_5$-alkenyloxy or $C_3-C_5$-alkynyloxy; and
$M^\oplus$ represents a cation equivalent of an alkali metal or alkaline earth metal; or of a nitrogen-containing base; and
B represents an imidazolone of the formula

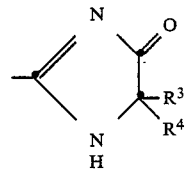

or

A and B together form a fused imidazolone of the formula

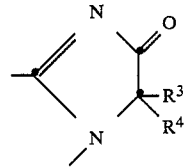

and
$R^3$ represents $C_1-C_4$-alkyl; and
$R^4$ represents a methyl or ethyl radical substituted by from 1 to 5 fluorine atoms.

Preferred compounds of formula I are those
in which
X represents CH or N;
$R^1$ and $R^2$ independently of one another represent hydrogen or $C_1-C_4$-alkyl; or
$R^1$ and $R^2$, together with the carbon atoms of the six-membered ring to which they are bonded, form a cyclopentene, cyclohexene, benzene or dihydropyran radical; and
A represents OH or $C_1-C_4$-alkoxy;
B represents an imidazolone of the formula

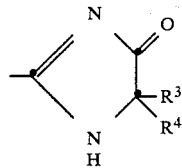

or

A and B together form a fused imidazolone of the formula

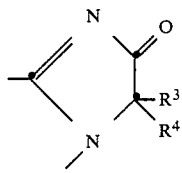

and
$R^3$ represents $C_1-C_4$-alkyl; and $R^4$ represents a methyl or ethyl radical substituted by from 1 to 5 fluorine atoms.

Especially preferred are the compounds of formula I in which X, $R^1$, $R^2$, A, and B and $R^3$ are as defined above and $R^4$ represents $CHF-CH_3$, $CF_3$ or $CHF_2$.

Prominence should be given also to the compounds of formula I in which X, $R^1$, $R^2$, A, B and $R^4$ are as defined above and $R^3$ represents methyl.

In addition, prominence is given to the compounds of formula I in which $R^2$ represents hydrogen and $R^1$ represents $C_1$–$C_4$-alkyl, especially methyl and ethyl, preferably ethyl.

Prominence should be given also to the compounds of formula I in which $R^1$ and $R^2$ together represent a $-(CH_2)_3-$, $-(CH_2)_4-$ or $-CH=CH-CH=CH-$ bridge.

The following are to be mentioned by name:

2-(5-methyl-5-trifluoromethylimidazol-4-on-2-yl)-isonicotinic acid, 2-(5-methyl-5-trifluoromethylimidazol-4-on-2-yl)-5-methylisonicotinic acid, 2-(5-methyl-5-trifluoromethylimidazol-4-on-2-yl)-5-ethylisonicotinic acid, 2-[5-(1-fluoroethyl)-5-methylimidazol-4-on-2-yl]-isonicotinic acid, 2-[5-(1-fluoroethyl)-5-methylimidazol-4-on-2-yl]-5-methylisonicotinic acid, 2-(5-methyl-5-trifluoromethylimidazol-4-on-2-yl)-quinoline-3-carboxylic acid, 2-[5-(1-fluoroethyl)-5-methylimidazol-4-on-2-yl]-5-ethylisonicotinic acid, 2-[5-difluoromethyl-5-methylimidazol-4-on-2-yl]-isonicotinic acid, 2-[5-difluoromethyl-5-methylimidazol-4-on-2-yl]-5-methylisonicotinic acid, 2-[5-difluoromethyl-5-methylimidazol-4-on-2-yl]-5-ethylisonicotinic acid, 2-[5-difluoromethyl-5-methylimidazol-4-on-2-yl]-5,6-dihydrocyclopenta-[b]pyridine-3-carboxylic acid, 2-[5-difluoromethyl-5-methylimidazol-4-on-2-yl]-5,6,7,8-tetrahydroquinoline-3-carboxylic acid, 2-[5-difluoromethyl-5-methylimidazol-4-on-2-yl]-quinoline-3-carboxylic acid, 2-[5-(1-fluoroethyl)-5-methylimidazol-4-on-2-yl]-5,6-dihydrocyclopenta[b]pyridine-3-carboxylic acid, 2-[5-(1-fluoroethyl)-5-methylimidazol-4-on-2-yl]-5,6,7,8-tetrahydroquinoline-3-carboxylic acid, 2-[5-(1-fluoroethyl)-5-methylimidazol-4-on-2-yl]-isonicotinic acid methyl ester, 2-[5-(1-fluoroethyl)-5-methylimidazol-4-on-2-yl]-isonicotinic acid ethyl ester and 2-[5-(1-fluoroethyl)-5-methylimidazol-4-on-2-yl]-5-ethylisonicotinic acid ethyl ester.

On the basis of their chemical structure, the compounds of formula I according to this Application may be defined as: imidazolones of formula Ia

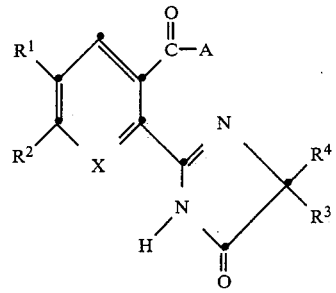

in which $R^1$, $R^2$, A, $R^3$ and $R^4$ are as defined above; or as fused imidazolones of formula Ib

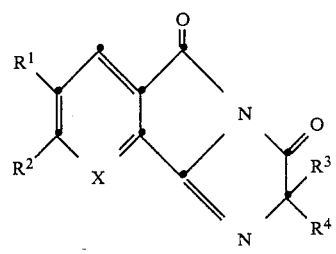

in which X, $R^1$, $R^2$, $R^3$ and $R^4$ are as defined above; or as fused imidazolones of formula Ic

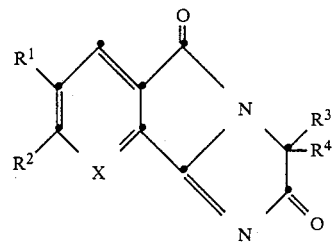

in which X, $R^1$, $R^2$, $R^3$ and $R^4$ are as defined above.

The compounds of formula I according to this Application can be prepared analogously to processes known from the literature. Depending on the structure of the desired end product of formula Ia, Ib or Ic, various processes known per se may be used.

The invention therefore relates also to processes for the preparation of compounds of formula Ia

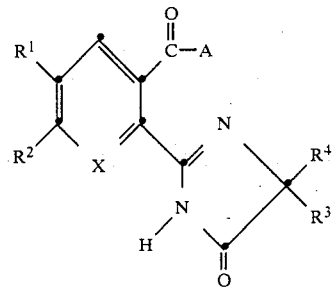

in which A represents OH and the radicals X, $R^1$, $R^2$, $R^3$ and $R^4$ are as defined above, characterised in that
(a) a diester of formula IV

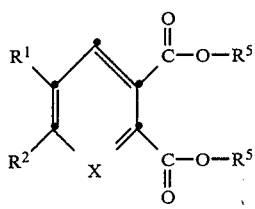

IV in which X, $R^1$ and $R^2$ are as defined above and the radicals $R^5$ independently of one another represent $C_1$–$C_6$-alkyl, is reacted with an α-amino acid amide of formula II in which $R^3$ and $R^4$ are defined as above

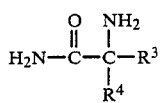

II in the presence of at least an equimolar amount of a base, and the reaction mixture is then worked up by hydrolysis.

The invention relates also to processes for the preparation of compounds of formula Ib

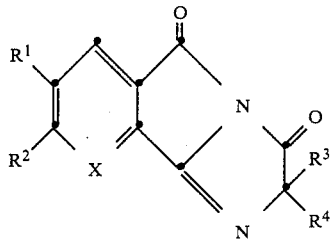

Ib in which the radicals X, $R^1$, $R^2$, $R^3$ and $R^4$ are as defined above, characterised in that (b) a compound of formula Ia

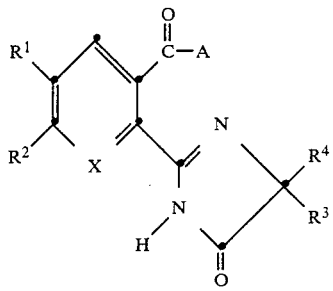

Ia in which X, $R^1$, $R^2$, $R^3$ and $R^4$ are as defined above and A represents OH, is cyclised in the presence of a water-binding or water-removing agent to give Ib.

In addition, the invention relates to processes for the preparation of compounds of formula Ic

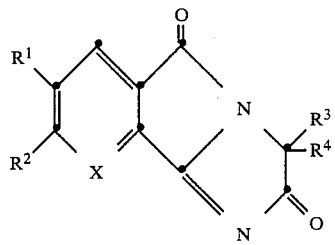

Ic in which X, $R^1$, $R^2$, $R^3$ and $R^4$ are as defined above, characterised in that (c) an acid anhydride of formula V

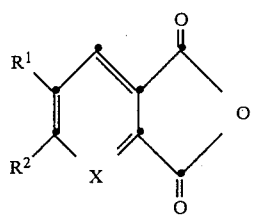

V in which $R^1$ and $R^2$ are as defined above, is reacted with an α-amino acid amide of formula II

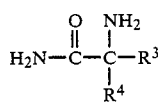

II in which $R^3$ and $R^4$ are as defined above, to give an imide of formula III

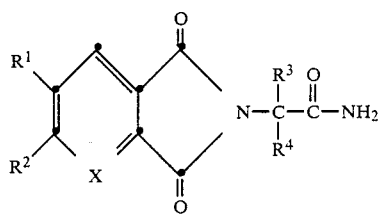

III and the imide of formula III so obtained is cyclised in the presence of at least a molar amount of a base to give Ic, or (d) a compound of formula Ib

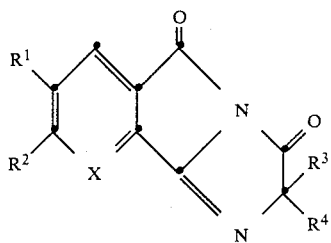

Ib in which X, $R^1$, $R^2$, $R^3$ and $R^4$ are as defined above, is isomerised under the action of an anhydrous protonic acid to give Ic.

The invention relates further to a process for the preparation of compounds of formula Ia

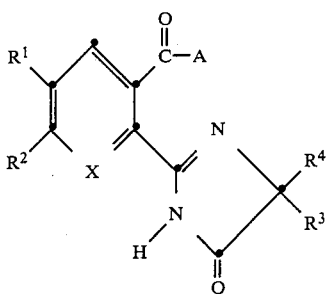

in which X, $R^1$, $R^2$, $R^3$ and $R^4$ are defined above and A represents $C_1$–$C_4$-alkoxy, $C_3$–$C_5$-alkenyloxy, $C_3$–$C_5$-alkynyloxy or $C_1$–$C_4$-alkoxy-$C_1$–$C_4$-alkoxy, characterised in that (e) a compound of formula Ib

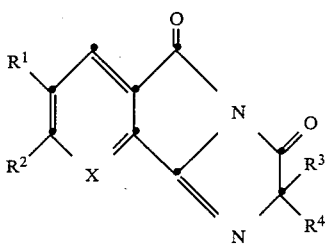

or a compound of formula Ic

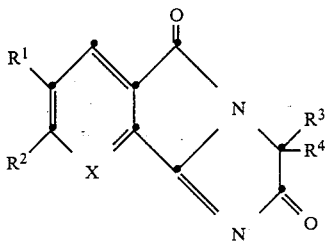

in which the radicals X, $R^1$, $R^2$, $R^3$ and $R^4$ are as defined above, is reacted with an alcohol of formula VI

H A                                                       VI, in which A represents $C_1$–$C_4$-alkoxy, $C_3$–$C_5$-alkenyloxy, $C_3$–$C_5$-alkynyloxy or $C_1$–$C_4$-alkoxy-$C_1$–$C_4$-alkoxy, if desired in the presence of an acid or base.

The invention includes also processes for the preparation of salts of formula Ia'

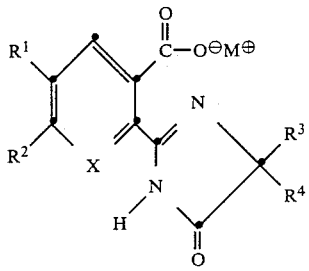

in which X, $R^1$, $R^2$, $R^3$ and $R^4$ are as defined above and $M^\oplus$ represents a cation equivalent of an alkali metal or alkaline earth metal or of a nitrogen-containing base, characterised in that (f) a compound of formula Ia

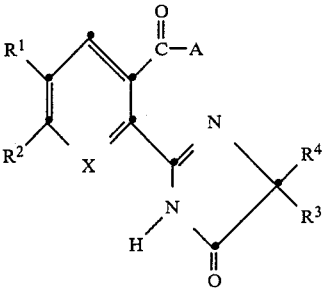

in which the radicals, X, $R^1$, $R^2$, $R^3$ and $R^4$ are as defined above and A represents OH, is reacted with an equivalent amount of a compound of formula VII $OH^\ominus M^\oplus$                                                       VII, in which $M^\oplus$ represents a cation equivalent of an alkali metal or alkaline earth metal or a quaternary nitrogen-containing base, or (g) a compound of formula Ia in which A represents OH is reacted directly with an alkali metal or alkaline earth metal or with an alkali metal salt or alkaline earth metal salt or the nitrogen-containing base.

Reactions that are analogous to the processes according to the invention, and the reaction conditions to be observed when carrying them out, such as selection of solvents and reactants, are known, for example, from the following patent publications: EP-A-0041623, EP-A-0212200, GB-A-2174395, DE-A-3420271, EP-A-0133309 and EP-A-0216360.

The reactions are generally carried out at from 0 to 180° C., preferably in a temperature range of from room temperature to the reflux temperature of the reaction mixtures.

The reactions are preferably carried out in the presence of solvents. Suitable solvents are especially those which are capable of dissolving the educts and/or products and which do not adversely affect the reaction.

Mention should be made of alcohols, such as methanol, ethanol, n-propanol, isopropanol, n-butanol, tert.-butanol, glyme, ethylene glycol etc.; ethers, such as diethyl ether, tetrahydrofuran, diglyme etc.; halogenated hydrocarbons, such as dichloromethane, trichloromethane, tetrachloromethane etc.; aromatic hydrocarbons, such as benzene, toluene, xylene, chlorobenzene, dichlorobenzene etc.; acid amides, such as dimethylformamide, acetamide, N-methylpyrrolidone; sulphoxides, such as dimethyl sulphoxide or sulpholane; or other solvents that are inert towards the reactants.

It is advantageous to carry out some of the above-mentioned reactions under anhydrous conditions (processes b, c, d and e), while in process f it is possible to use water alone as solvent or water/solvent mixtures.

Suitable bases are, inter alia, alcoholates, amines, hydrides, amides or organometal compounds.

Protonic acids are hydrohalic acids, sulphuric acid, phosphoric acid etc.

As water-binding agent there has proved suitable dicyclohexylcarbodiimide (DCC), especially the DCC/dichloromethane system.

Suggested water-removing agents are, inter alia, those employed in the process steps for removing water using azeotropic mixtures, such as, for example, toluene/water, that are customary in preparative chemistry.

The starting compounds of formulas IV and V are known or can be prepared analogously to processes known from the literature. Reference is made especially to the following patent publications, and to the literature cited therein: EP-A-0041623, EP-A-0212200, GB-A-2174395, DE-A-3420271, EP-A-0133309, EP-A-0216360, EP-A-0172140, and to Swiss Patent Application CH 2301/87-1 of 18th June 1987 which has not yet been published.

The α-amino acid amides of formula II are novel. They are suitable as intermediates especially for the synthesis of the compounds of formula I according to the invention, making a considerable contribution to the structure thereof.

The invention therefore relates also to the novel α-amino acid amides of formula II

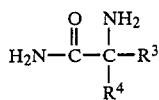
II in which
$R^3$ represents $C_1$–$C_4$-alkyl and
$R^4$ represents a methyl or ethyl radical substituted by from 1 to 5 fluorine atoms.

The α-amino acid amides of formula II may be in various stereoisomeric forms. The invention relates both to the racemic forms and to the various stereoisomeric forms.

The α-amino acid amides of formula II can be prepared analogously to methods known from the literature.

They can be prepared especially be amidation of amino acids of formula VIII

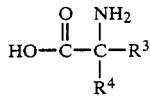
VIII in which $R^3$ and $R^4$ are as defined above, for example in accordance with the reaction scheme below

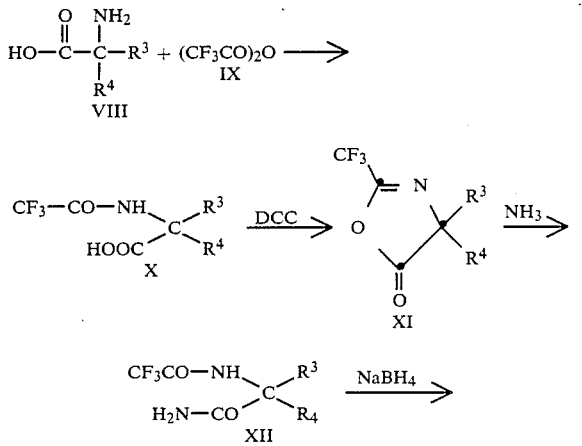

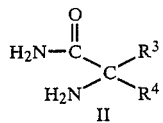
II by reaction of the amino acid VIII with trifluoroacetic acid anhydride IX to give the N-protected compound X, and subsequent cyclisation with dicyclohexylcarbodiimide (DCC) to give the oxazolidinone XI, which reacts with $NH_3$, with ring-opening, to give the amide XII. The trifluoroacetyl protecting group can then be removed from XII, for example using $NaBH_4$ (analogously to Jones et al., J. Chem. Soc. 1965, 6227–6239 and E. Wünsch in Houben-Weyl, Vol. 15/1, p. 177 ff).

The α-amino acid amides II are also generally accessible by the Strecker synthesis in accordance with the following reaction scheme

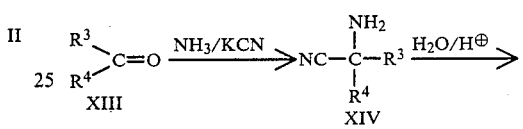

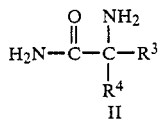
II in which, starting from the ketone of formula XIII in which $R^3$ and $R^4$ are as defined above, the nitrile XIV is obtainable by the addition of ammonia and cyanide, from which nitrile XIV the α-amino acid amide II can be prepared by hydrolysis (for example, in accordance with Biochim. Biophys. Acta 74 (1963) 386–391).

The fluorinated ketones of formula XIII required for this process are known or can be synthesised analogously to processes known from the literature (for example by Grignard reactions analogously to Olah, Chem. Ber. 89 [1956], 864 or Haszeldine, J. Chem. Soc. 1954, 1273).

The amino acids of formula VIII are likewise known or can be prepared analogously to processes known from the literature. The invention relates also to the novel amino acids VIII, the novel ketones XIII and the compounds of formula XIV.

For example, the amino acids of formula VIII can be obtained by fluorination of correspondingly substituted β-hydroxyamino acids XIX with $HF/SF_4$ at low temperatures (analogously to Kollonitsch; J. Org. Chem. 44 [1979], 771–777 and J. Org. Chem. 40 [1975], 3808–3809). This process is especially suitable for the preparation of compounds of formula VIIIa in which $R^4$ represents a radical of formula $R^6$ CHF (where $R^6 = CH_3$, $CH_2F$, $CHF_2$ and $CF_3$).

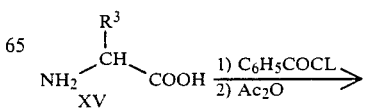

-continued

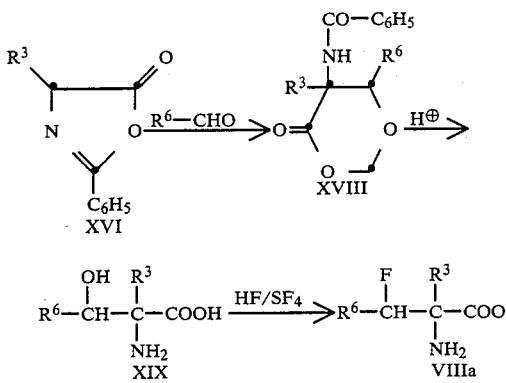

The starting materials for this process are amino acids of formula XV, which are cyclised with benzoyl chloride and acetic anhydride to give the oxazolone XVI, which is then rearranged by reaction with an aldehyde XVII to give XVIII. The β-hydroxyamino acid XIX can then be obtained by the action of an acid (analogously to Kaminski, Synthesis 1973, 792–794).

The α-aminoacid of formula VIIIa can as well be obtained by a varient of the Erlenmayer azlacton synthesis (according to F. Heinzer and D. Bellus, Helv. Chim. Acta 64 (1981) 2279) by reacting the isocyanoacetic acid ester ($R^7 = C_1$–$C_4$-alkyl) XXIII with the aldehyde·$R^6$ CHO to yield the oxazoline XXIV which reacts with water upon to the β-hydroxyaminoacid XIX. The amino-acid XIX is then fluorinated as shown above.

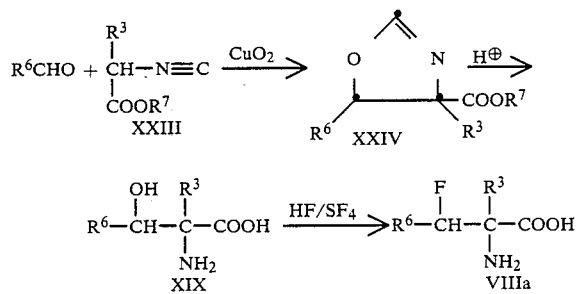

The amino acids of formula VIII can also be prepared by reaction of the Schiff base XX in which R' represents $C_1$–$C_4$-alkyl.

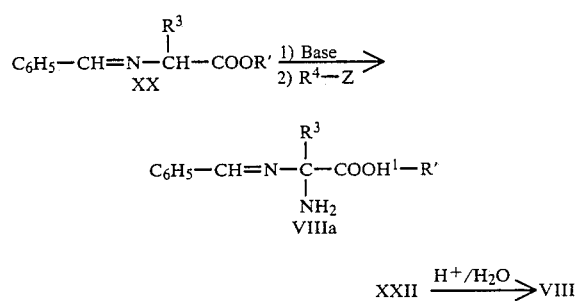

The compound of formula XX reacts under the action of a base with the compound XXI in which Z represents a nucleofugal group, such as chlorine or bromine, to give the ester XXII, from which VIII can be obtained by acid hydrolysis (analogously to Bey et al., J. Org. Chem. 44 [1979], 2732).

The invention relates also to herbicidal compositions containing at least one compound of formula I as active ingredient, to the use of compounds of formula I in methods of controlling weeds and grasses pre- and/or post-emergence, and to the preparation of herbicidal compositions containing compounds of formula I.

The compounds of formula I are generally used successfully at rates of application of from 0.005 to 5 kg/ha, especially from 0.05 to 4.0 kg/ha, most especially from 0.1 to 2.0 kg/ha. The optimum amount of active ingredient for the particular purpose and time of application when used pre-emergence or post-emergence can be determined by tests. In addition, the compounds of formula I can also be applied to the seeds of the particular cultivated plant (seed dressing).

The compounds of formula I are proposed for use in crops of useful plants, especially in cereals, cotton, soybeans, maize, rice and sorghum. The compounds of formula I are distinguished by selectivity in cereals, leguminosae and soybeans.

The herbicidally active compounds of formula I can also be applied to the seeds of the useful plant crop (seed dressing). The active ingredient is then applied to the field when the useful plant is sown. The invention relates also to the seeds treated with the herbicidally active compound of formula I.

The compounds of formula I are used in unmodified form or, preferably, as compositions together with the adjuvants conventionally employed in the art of formulation, and are therefore formulated in known manner e.g. into emulsifiable concentrates, directly sprayable or dilutable solutions, dilute emulsions, wettable powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and contain a $C_8$-$C_{22}$-alkyl radical which also includes the alkyl moiety of acyl radicals, e.g. the sodium or calcium salt of lignosulphonic acid, of dodecylsulphate or of a mixture of fatty alcohol sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde.

Also suitable are corresponding phosphates, e.g. salts of the phosphoric acid ester of an adduct of p-nonylphenol with 4 to 14 moles of ethylene oxide; or phospholipids.

Non-ionic surfactants are preferably polyglycol ether and polyglycol ester derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$-alkyl radical and, as further substituents, unsubstituted or halogenated lower alkyl, benzyl or hydroxy-lower alkyl radicals. The salts are preferably in the form of halides, methylsulphates or ethylsulphates, e.g. stearyltrimethylammonium chloride or benzyldi(2-chloroethyl)ethylammonium bromide.

The surfactants customarily employed in the art of formulation are described e.g. in the following publications:

"1986 International McCutcheon's Emulsifiers & Detergents", Glen Rock, N.J. USA, 1986, Dr. Helmut Stache, "Tensid Taschenbuch", Carl Hanser Verlag, Munich/Vienna, 1981.

The herbicidal compositions usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

EMULSIFIABLE CONCENTRATES compound of formula I: 1 to 20%, preferably 5 to 10%
surfactant: 5 to 30%, preferably 10 to 20%
liquid carrier: 50 to 94%, preferably 70 to 85%

DUSTS compound of formula I: 0.1 to 10%, preferably 0.1 to 1%
solid carrier: 99.9 to 90%, preferably 99.9 to 99%

SUSPENSION CONCENTRATE compound of formula I: 5 to 75%, preferably 10 to 50%
water: 94 to 25%, preferably 90 30%
surfactant: 1 to 40%, preferably 2 to 30%

WETTABLE POWDERS compound of formula I: 0.5 to 90%, preferably, 1 to 80%
surfactant: 0.5 to 20%, preferably 1 to 15%
solid carrier: 5 to 95%, preferably 15 to 90%

GRANULATES compound of formula I: 0.5 to 30%, preferably 3 to 15%
solid carrier: 99.5 to 70%, preferably 97 to 85%.

Whereas commercial products will preferably be formulated as concentrates, the end user will normally employ dilute formulations. The formulations can be diluted to a concentration as low as 0.001% of active ingredient. The rates of application are normally from 0.005 to 5 kg a.i./ha.

The compositions may also contain further auxiliaries such as stabilisers, antifoams, viscosity regulators, binders, tackifiers as well as fertilisers or other active ingredients for obtaining special effects.

The following Examples illustrate the subject of the invention.

EXAMPLE 1

2-amino-3-fluoro-2-methylbutyric acid 40 g (0.3 mol) of 2-amino-3-hydroxy-2-methylbutyric acid are introduced into a Monel boiler cooled to −56° C. using dry ice/acetone. 400 g (20 mol) of hydrofluoric acid are then introduced by condensation. When the exothermic reaction has subsided, 106 g (1 mol) of sulphur tetrafluoride are added in portions with stirring.

The reaction mixture is then stirred for a further 22 hours at −66° C. and a pressure of 2×10⁵ Pascal and is then concentrated in a rotary evaporator. The residue so obtained is purified on an ion exchanger (Dowex 50 W×8 150–200 mesh) using water and 1 molar hydrochloric acid as eluants. The aqueous solution so obtained is concentrated to dryness, taken up in 150 ml of ethanol and precipitated by the addition of 100 ml of propylene chloride. The product is filtered off and dried in vacuo at 50° C.

23.6 g (58.1%) of the title compound of formula

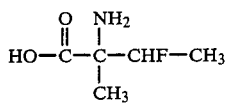

are isolated in the form of a white powder having a melting point of 226° C.

EXAMPLE 2

3-fluoro-2-methyl-2-trifluoroacetaminobutyric acid 1.35 g (10 mmol) of the 2-amino-3-fluoro-2methylbutyric acid obtainable in accordance with Example 1 are introduced in portions into 6.5 g (31 mmol) of trifluoroacetic acid anhydride with stirring at room temperature. The mixture is stirred for a further 2 hours at room temperature and then concentrated to dryness at 25° C. in a rotary evaporator. The residue is taken up in 20 ml of ice-water to which a drop of pyridine has been added, and is then extracted with diethyl ether.

Concentration of the organic phase by evaporation yields an oil that slowly crystallises.

1.8 g (78.3% of the title compound of formula

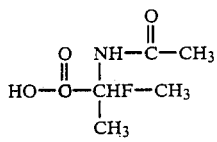

are isolated in the form of crystals having a melting point of 25°–30° C.

Elementary analysis [%]:
calc.: C: 36.37, H: 3.93, N: 6.06, F: 32.88.
found: C: 36.42, H: 3.94, N: 6.03, F: 32.50.

EXAMPLE 3a 2-amino-3-fluoro-2-methylbutyric acid amide

A solution of 20.6 g (0.1 mol) of N,N′-dicyclohexylcarbodiimide in 50 ml of dichloromethane is added dropwise at 25°–30° C., with stirring, to a solution of 23.1 g (0.1 mol) of 3-fluoro-2-methyl2-trifluoroacetaminobutyric acid (obtainable in accordance with Example 2) in 200 ml of dichloromethane. After 2 ours, ammonia gas is introduced at 25° C. until the suspension remains alkaline over a long period of time. After filtering and concentrating the solvent by evaporation, there are obtained 23 g of a brown oil, which is dissolved in 200 ml of ethanol. 15.1 g of 0.4M sodium borohydride are added in portions thereto at 25°–30° C. with stirring. After a further 5 hours, 100 ml of acetone are added dropwise with cooling, and after a further hour the whole is concentrated to dryness in a rotary evaporator. 100 ml of water are added to the residue and the whole is extracted with dichloromethane. The product is obtained from the dried organic phase after concentration.

11.7 g 87.3%) of the title compound of formula

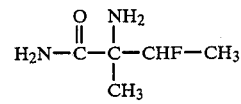

are isolated in the form of a yellow oil.

EXAMPLE 3b

Separation of a diastereoisomer of 2-amino-3-fluoro-2-methyl-butyric acid amide 11.7 g of the diastereoisomeric mixture obtainable in accordance with Example 3a in the form of a yellow oil are separated by recrystallisation from ethyl acetate/petroleum ether (95.5).

1.2 g (8.9%) of a pure diastereoisomer of the title compound are isolated in the form of crystals having a melting point of 81° C.

7.1 g (53%) of the diastereoisomeric mixture are recovered in the form of a light-yellow wax by concentration of the mother liquor.

EXAMPLE 3c 2-amino-3,3-difluoro-2-methylpropionic acid amide

Starting from 2-amino-3,3-difluoro-2-methylpropionic acid (Bey et al., J. Org. Chem., 44 [1979], 2732) there is obtained analogously to Example 3a the title compound of formula

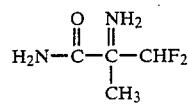

in the form of crystals having a melting point of 77°–80° C.

EXAMPLE 4

2-amino-2-trifluoromethylpropionic acid amide

In a bomb tube, 19.2 ml (0.2 mol) of 1,1,1-trifluoroacetone are added dropwise to a suspension of 13 g (0.2 mol) of potassium cyanide in 10 ml of water, while cooling with ice. The mixture is then stirred for 15 minutes at 70° C. with the tube closed. 25 ml of 25% ammonia solution are then added dropwise while cooling with ice, and the mixture is stirred for a further 5 hours at 100° C. with the tube closed.

Concentration of the reaction mixture by evaporation yields a dark brown oil from which the product is obtained by sublimation at 140° C. and 13 Pascal and subsequent recrystallisation using ethyl acetate.

1.7 g (6.0%) of the title compound of formula

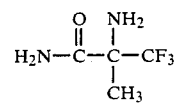

are isolated in the form of a white powder having a melting point of 84°–85° C.

EXAMPLE 5

2-(5-methyl-5-trifluoromethyl-1H-imidazol-4-on-2-yl)pyridine-3carboxylic acid 1.5 g (13.4 mmol) of potassium tert.-butoxide are added in portions at 60°–80° C. to a solution of 1.0 g (6.4 mmol) of 2-amino-2-trifluoromethylpropionic acid amide (obtainable in accordance with Example 4) and 1.43 g (6.4 mmol) of pyridine-2,3-dicarboxylic acid diethyl ester in 20 ml of toluene. After 2 hours, the potassium salt is filtered off, washed with ether and taken up in 15 ml of water. The solution is adjusted to pH 4.5 with 2 molar hydrochloric acid and extracted with ethyl acetate. The organic phase is dried and concentrated, and the residue is recrystallised from ethyl acetate.

0.55 g (30%) of the title compound of formula

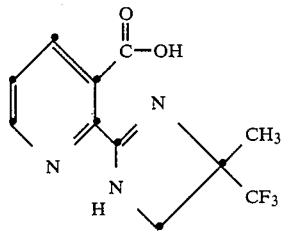

Comp. No. 1.001 is isolated in the form of a light-beige powder having a melting point of 180°–184° C.

The carboxylic acids of formula Ia given in Table 1 below can be prepared in accordance with Example 5.

TABLE 1

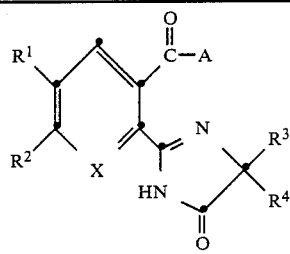

Ia

| Comp. no. | A | X | $R^1$ | $R^2$ | $R^3$ | $R^4$ | m.p. [°C.] phys. data |
|---|---|---|---|---|---|---|---|
| 1.001 | OH | N | H | H | $CH_3$ | $CF_3$ | 180–184 |
| 1.002 | OH | N | $CH_3$ | H | $CH_3$ | $CF_3$ | 225–226 |
| 1.003 | OH | N | $C_2H_5$ | H | $CH_3$ | $CF_3$ | 223–225 |
| 1.004 | OH | N | n-$C_3H_7$ | H | $CH_3$ | $CF_3$ | |
| 1.005 | OH | N | iso-$C_3H_7$ | H | $CH_3$ | $CF_3$ | |
| 1.006 | OH | N | n-$C_4H_9$ | H | $CH_3$ | $CF_3$ | |
| 1.007 | OH | N | —$(CH_2)_3$— | | $CH_3$ | $CF_3$ | |
| 1.008 | OH | N | —$(CH_2)_4$— | | $CH_3$ | $CF_3$ | |
| 1.009 | OH | N | —$CH_2OCH_2CH_2$— | | $CH_3$ | $CF_3$ | |
| 1.010 | OH | N | —CH=CH—CH=CH— | | $CH_3$ | $CF_3$ | 200–204 |
| 1.011 | OH | N | $C_2H_5$ | $CH_3$ | $CH_3$ | $CF_3$ | |
| 1.012 | OH | CH | H | H | $CH_3$ | $CF_3$ | |
| 1.013 | OH | CH | $CH_3$ | H | $CH_3$ | $CF_3$ | |
| 1.014 | OH | CH | H | $CH_3$ | $CH_3$ | $CF_3$ | |
| 1.015 | OH | N | H | H | $CH_3$ | $CHF_2$ | 188–190 |
| 1.016 | OH | N | $CH_3$ | H | $CH_3$ | $CHF_2$ | 236–238 |
| 1.017 | OH | N | $C_2H_5$ | H | $CH_3$ | $CHF_2$ | 197–199 |
| 1.018 | OH | N | n-$C_3H_7$ | H | $CH_3$ | $CHF_2$ | |
| 1.019 | OH | N | iso-$C_3H_7$ | H | $CH_3$ | $CHF_2$ | |
| 1.020 | OH | N | n-$C_4H_9$ | H | $CH_3$ | $CHF_2$ | |
| 1.021 | OH | N | —$(CH_2)_3$— | | $CH_3$ | $CHF_2$ | 161–168 |
| 1.022 | OH | N | —$(CH_2)_4$— | | $CH_3$ | $CHF_2$ | 215–218 |
| 1.023 | OH | N | —$CH_2OCH_2CH_2$— | | $CH_3$ | $CHF_2$ | |
| 1.024 | OH | N | —CH=CH—CH=CH— | | $CH_3$ | $CHF_2$ | 236–238 |
| 1.025 | OH | N | $C_2H_5$ | $CH_3$ | $CH_3$ | $CHF_2$ | |
| 1.026 | OH | CH | H | H | $CH_3$ | $CHF_2$ | |
| 1.027 | OH | CH | $CH_3$ | H | $CH_3$ | $CHF_2$ | |
| 1.028 | OH | CH | H | $CH_3$ | $CH_3$ | $CHF_2$ | |
| 1.029 | OH | N | H | H | $CH_3$ | $CH_2F$ | |
| 1.030 | OH | N | $CH_3$ | H | $CH_3$ | $CH_2F$ | |
| 1.031 | OH | N | $C_2H_5$ | H | $CH_3$ | $CH_2F$ | |
| 1.032 | OH | N | n-$C_3H_7$ | H | $CH_3$ | $CH_2F$ | |
| 1.033 | OH | N | iso-$C_3H_7$ | H | $CH_3$ | $CH_2F$ | |
| 1.034 | OH | N | n-$C_4H_9$ | H | $CH_3$ | $CH_2F$ | |
| 1.035 | OH | N | —$(CH_2)_3$— | | $CH_3$ | $CH_2F$ | |
| 1.036 | OH | N | —$(CH_2)_4$— | | $CH_3$ | $CH_2F$ | |
| 1.037 | OH | N | —$CH_2OCH_2CH_2$— | | $CH_3$ | $CH_2F$ | |
| 1.038 | OH | N | —CH=CH—CH=CH— | | $CH_3$ | $CH_2F$ | |
| 1.039 | OH | N | $C_2H_5$ | $CH_3$ | $CH_3$ | $CH_2F$ | |
| 1.040 | OH | CH | H | H | $CH_3$ | $CH_2F$ | |
| 1.041 | OH | CH | $CH_3$ | H | $CH_3$ | $CH_2F$ | |
| 1.042 | OH | CH | H | $CH_3$ | $CH_3$ | $CH_2F$ | |
| 1.043 | OH | N | H | H | $CH_3$ | $CHFCH_3$ | 126–130 |
| 1.044 | OH | N | $CH_3$ | H | $CH_3$ | $CHFCH_3$ | 206–207 |
| 1.045 | OH | N | $C_2H_5$ | H | $CH_3$ | $CHFCH_3$ | 167–169 |

TABLE 1-continued

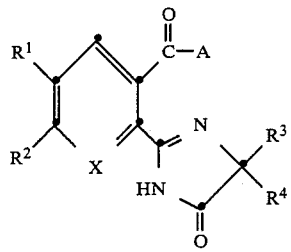

Ia

| Comp. no. | A | X | R¹ | R² | R³ | R⁴ | m.p. [°C.] phys. data |
|---|---|---|---|---|---|---|---|
| 1.046 | OH | N | n-C₃H₇ | H | CH₃ | CHFCH₃ | |
| 1.047 | OH | N | iso-C₃H₇ | H | CH₃ | CHFCH₃ | |
| 1.048 | OH | N | n-C₄H₉ | H | CH₃ | CHFCH₃ | |
| 1.049 | OH | N | —(CH₂)₃— | | CH₃ | CHFCH₃ | 118–123 |
| 1.050 | OH | N | —(CH₂)₄— | | CH₃ | CHFCH₃ | 117–132 |
| 1.051 | OH | N | —CH₂OCH₂CH₂— | | CH₃ | CHFCH₃ | |
| 1.052 | OH | N | —CH=CH—CH=CH— | | CH₃ | CHFCH₃ | 228–231 |
| 1.053 | OH | N | C₂H₅ | CH₃ | CH₃ | CHFCH₃ | |
| 1.054 | OH | CH | H | H | CH₃ | CHFCH₃ | |
| 1.055 | OH | CH | CH₃ | H | CH₃ | CHFCH₃ | |
| 1.056 | OH | CH | H | CH₃ | CH₃ | CHFCH₃ | |
| 1.057 | OH | N | H | H | C₂H₅ | CF₃ | |
| 1.058 | OH | N | CH₃ | H | C₂H₅ | CF₃ | |
| 1.059 | OH | CH | H | H | C₂H₅ | CF₃ | |
| 1.060 | OH | N | C₂H₅ | H | C₂H₅ | CHF₂ | |
| 1.061 | OH | N | n-C₃H₇ | H | C₂H₅ | CHF₂ | |
| 1.062 | OH | N | iso-C₃H₇ | H | C₂H₅ | CH₂F | |
| 1.063 | OH | N | n-C₄H₉ | H | C₂H₅ | CH₂F | |
| 1.064 | OH | CH | CH₃ | H | C₂H₅ | CH₂F | |
| 1.065 | OH | N | —(CH₂)₃— | | C₂H₅ | CHFCH₃ | |
| 1.066 | OH | N | —(CH₂)₄— | | C₂H₅ | CHFCH₃ | |
| 1.067 | OH | N | —CH₂OCH₂CH₂— | | C₂H₅ | CHFCH₃ | |
| 1.068 | OH | N | —CH=CH—CH=CH— | | C₂H₅ | CHFCH₃ | |
| 1.069 | OH | CH | H | CH₃ | C₂H₅ | CHFCH₃ | |
| 1.070 | OH | N | C₂H₅ | H | n-C₃H₇ | CF₃ | |
| 1.071 | OH | N | n-C₃H₇ | H | n-C₃H₇ | CF₃ | |
| 1.072 | OH | N | iso-C₃H₇ | H | n-C₃H₇ | CHF₂ | |
| 1.073 | OH | N | n-C₄H₉ | H | n-C₃H₇ | CHF₂ | |
| 1.074 | OH | N | —(CH₂)₃— | | n-C₃H₇ | CH₂F | |
| 1.075 | OH | N | —(CH₂)₄— | | n-C₃H₇ | CH₂F | |
| 1.076 | OH | N | H | H | n-C₃H₇ | CHFCH₃ | |
| 1.077 | OH | N | CH₃ | H | n-C₃H₇ | CHFCH₃ | |
| 1.078 | OH | N | —CH₂OCH₂CH₂— | | n-C₃H₇ | CHFCH₃ | |
| 1.079 | OH | N | —CH=CH—CH=CH— | | n-C₃H₇ | CHFCH₃ | |
| 1.080 | OH | N | iso-C₃H₇ | H | i-C₃H₇ | CF₃ | |
| 1.081 | OH | N | n-C₄H₉ | H | i-C₃H₇ | CF₃ | |
| 1.082 | OH | N | —(CH₂)₃— | | i-C₃H₇ | CHF₂ | |
| 1.083 | OH | N | —(CH₂)₄— | | i-C₃H₇ | CHF₂ | |
| 1.084 | OH | N | —CH₂OCH₂CH₂— | | i-C₃H₇ | CH₂F | |
| 1.085 | OH | N | —CH=CH—CH=CH— | | i-C₃H₇ | CH₂F | |
| 1.086 | OH | N | H | H | i-C₃H₇ | CHFCH₃ | |
| 1.087 | OH | N | CH₃ | H | i-C₃H₇ | CHFCH₃ | |
| 1.088 | OH | N | C₂H₅ | H | i-C₃H₇ | CHFCH₃ | |
| 1.089 | OH | N | n-C₃H₇ | H | i-C₃H₇ | CHFCH₃ | |
| 1.090 | OH | N | —(CH₂)₃— | | n-C₄H₉ | CF₃ | |
| 1.091 | OH | N | —(CH₂)₄— | | n-C₄H₉ | CF₃ | |
| 1.092 | OH | N | —CH₂OCH₂CH₂— | | n-C₄H₉ | CHF₂ | |
| 1.093 | OH | N | —CH=CH—CH=CH— | | n-C₄H₉ | CHF₂ | |
| 1.094 | OH | N | C₂H₅ | CH₃ | n-C₄H₉ | CH₂F | |
| 1.095 | OH | CH | H | H | n-C₄H₉ | CH₂F | |
| 1.096 | OH | N | H | H | n-C₄H₉ | CHFCH₃ | |
| 1.097 | OH | N | CH₃ | H | n-C₄H₉ | CHFCH₃ | |
| 1.098 | OH | N | C₂H₅ | H | CH₃ | CHFCH₃ | 174–175* |

*Compound no. 1.098 can be prepared analogously to Example 5 using the diastereoisomers according to Example 3b.

EXAMPLE 6

General process for the preparation of compounds of formula Ib

A solution of a carboxylic acid of formula is (A=OH) in dichloromethane is stirred for approximately one hour with a 1.1 molar amount of dicyclohexylcarbodiimide. The precipitated dicyclohexylurea is then filtered off, the filtrate is concentrated and, if necessary, the product of formula Ib is purified by crystallisation.

The compounds of formula Ib given in Table 2 below can be prepared in accordance with Example 6.

TABLE 2

Compounds of formula Ib

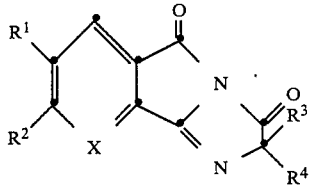

| Comp. no. | X | $R^1$ | $R^2$ | $R^3$ | $R^4$ | m.p. [°C.] phys. data |
|---|---|---|---|---|---|---|
| 2.001 | N | H | H | $CH_3$ | $CF_3$ | |
| 2.002 | N | $CH_3$ | H | $CH_3$ | $CF_3$ | |
| 2.003 | N | $C_2H_5$ | H | $CH_3$ | $CF_3$ | |
| 2.004 | N | $n$-$C_3H_7$ | H | $CH_3$ | $CF_3$ | |
| 2.005 | N | iso-$C_3H_7$ | H | $CH_3$ | $CF_3$ | |
| 2.006 | N | $n$-$C_4H_9$ | H | $CH_3$ | $CF_3$ | |
| 2.007 | N | —$(CH_2)_3$— | | $CH_3$ | $CF_3$ | |
| 2.008 | N | —$(CH_2)_4$— | | $CH_3$ | $CF_3$ | |
| 2.009 | N | —$CH_2OCH_2CH_2$— | | $CH_3$ | $CF_3$ | |
| 2.010 | N | —CH=CH—CH=CH— | | $CH_3$ | $CF_3$ | |
| 2.011 | N | $C_2H_5$ | $CH_3$ | $CH_3$ | $CF_3$ | |
| 2.012 | CH | H | H | $CH_3$ | $CF_3$ | |
| 2.013 | CH | $CH_3$ | H | $CH_3$ | $CF_3$ | |
| 2.014 | CH | H | $CH_3$ | $CH_3$ | $CF_3$ | |
| 2.015 | N | H | H | $CH_3$ | $CHF_2$ | |
| 2.016 | N | $CH_3$ | H | $CH_3$ | $CHF_2$ | |
| 2.017 | N | $C_2H_5$ | H | $CH_3$ | $CHF_2$ | |
| 2.018 | N | $n$-$C_3H_7$ | H | $CH_3$ | $CHF_2$ | |
| 2.019 | N | iso-$C_3H_7$ | H | $CH_3$ | $CHF_2$ | |
| 2.020 | N | $n$-$C_4H_9$ | H | $CH_3$ | $CHF_2$ | |
| 2.021 | N | —$(CH_2)_3$— | | $CH_3$ | $CHF_2$ | |
| 2.022 | N | —$(CH_2)_4$— | | $CH_3$ | $CHF_2$ | |
| 2.023 | N | —$CH_2OCH_2CH_2$— | | $CH_3$ | $CHF_2$ | |
| 2.024 | N | —CH=CH—CH=CH— | | $CH_3$ | $CHF_2$ | |
| 2.025 | N | $C_2H_5$ | $CH_3$ | $CH_3$ | $CHF_2$ | |
| 2.026 | CH | H | H | $CH_3$ | $CHF_2$ | |
| 2.027 | CH | $CH_3$ | H | $CH_3$ | $CHF_2$ | |
| 2.028 | CH | H | $CH_3$ | $CH_3$ | $CHF_2$ | |
| 2.029 | N | H | H | $CH_3$ | $CH_2F$ | |
| 2.030 | N | $CH_3$ | H | $CH_3$ | $CH_2F$ | |
| 2.031 | N | $C_2H_5$ | H | $CH_3$ | $CH_2F$ | |
| 2.032 | N | $n$-$C_3H_7$ | H | $CH_3$ | $CH_2F$ | |
| 2.033 | N | iso-$C_3H_7$ | H | $CH_3$ | $CH_2F$ | |
| 2.034 | N | $n$-$C_4H_9$ | H | $CH_3$ | $CH_2F$ | |
| 2.035 | N | —$(CH_2)_3$— | | $CH_3$ | $CH_2F$ | |
| 2.036 | N | —$(CH_2)_4$— | | $CH_3$ | $CH_2F$ | |
| 2.037 | N | —$CH_2OCH_2CH_2$— | | $CH_3$ | $CH_2F$ | |
| 2.038 | N | —CH=CH—CH=CH— | | $CH_3$ | $CH_2F$ | |
| 2.039 | N | $C_2H_5$ | $CH_3$ | $CH_3$ | $CH_2F$ | |
| 2.040 | CH | H | H | $CH_3$ | $CH_2F$ | |
| 2.041 | CH | $CH_3$ | H | $CH_3$ | $CH_2F$ | |
| 2.042 | CH | H | $CH_3$ | $CH_3$ | $CH_2F$ | |
| 2.043 | N | H | H | $CH_3$ | $CHFCH_3$ | |
| 2.044 | N | $CH_3$ | H | $CH_3$ | $CHFCH_3$ | |
| 2.045 | N | $C_2H_5$ | H | $CH_3$ | $CHFCH_3$ | |
| 2.046 | N | $n$-$C_3H_7$ | H | $CH_3$ | $CHFCH_3$ | |
| 2.047 | N | iso-$C_3H_7$ | H | $CH_3$ | $CHFCH_3$ | |
| 2.048 | N | $n$-$C_4H_9$ | H | $CH_3$ | $CHFCH_3$ | |
| 2.049 | N | —$(CH_2)_3$— | | $CH_3$ | $CHFCH_3$ | |
| 2.050 | N | —$(CH_2)_4$— | | $CH_3$ | $CHFCH_3$ | |
| 2.051 | N | —$CH_2OCH_2CH_2$— | | $CH_3$ | $CHFCH_3$ | |
| 2.052 | N | —CH=CH—CH=CH— | | $CH_3$ | $CHFCH_3$ | |
| 2.053 | N | $C_2H_5$ | $CH_3$ | $CH_3$ | $CHFCH_3$ | |
| 2.054 | CH | H | H | $CH_3$ | $CHFCH_3$ | |
| 2.055 | CH | $CH_3$ | H | $CH_3$ | $CHFCH_3$ | |
| 2.056 | CH | H | $CH_3$ | $CH_3$ | $CHFCH_3$ | |
| 2.057 | N | H | H | $C_2H_5$ | $CF_3$ | |
| 2.058 | N | $CH_3$ | H | $C_2H_5$ | $CF_3$ | |
| 2.059 | CH | H | H | $C_2H_5$ | $CF_3$ | |
| 2.060 | N | $C_2H_5$ | H | $C_2H_5$ | $CHF_2$ | |
| 2.061 | N | $n$-$C_3H_7$ | H | $C_2H_5$ | $CHF_2$ | |
| 2.062 | N | iso-$C_3H_7$ | H | $C_2H_5$ | $CH_2F$ | |
| 2.063 | N | $n$-$C_4H_9$ | H | $C_2H_5$ | $CH_2F$ | |
| 2.064 | CH | $CH_3$ | H | $C_2H_5$ | $CH_2F$ | |
| 2.065 | N | —$(CH_2)_3$— | | $C_2H_5$ | $CHFCH_3$ | |
| 2.066 | N | —$(CH_2)_4$— | | $C_2H_5$ | $CHFCH_3$ | |
| 2.067 | N | —$CH_2OCH_2CH_2$— | | $C_2H_5$ | $CHFCH_3$ | |
| 2.068 | N | —CH=CH—CH=CH— | | $C_2H_5$ | $CHFCH_3$ | |
| 2.069 | CH | H | $CH_3$ | $C_2H_5$ | $CHFCH_3$ | |

TABLE 2-continued

Compounds of formula Ib

| Comp. no. | X | $R^1$ | $R^2$ | $R^3$ | $R^4$ | m.p. [°C.] phys. data |
|---|---|---|---|---|---|---|
| 2.070 | N | $C_2H_5$ | H | $n-C_3H_7$ | $CF_3$ | |
| 2.071 | N | $n-C_3H_7$ | H | $n-C_3H_7$ | $CF_3$ | |
| 2.072 | N | $iso-C_3H_7$ | H | $n-C_3H_7$ | $CHF_2$ | |
| 2.073 | N | $n-C_4H_9$ | H | $n-C_3H_7$ | $CHF_2$ | |
| 2.074 | N | $-(CH_2)_3-$ | | $n-C_3H_7$ | $CH_2F$ | |
| 2.075 | N | $-(CH_2)_4-$ | | $n-C_3H_7$ | $CH_2F$ | |
| 4.076 | N | H | H | $n-C_3H_7$ | $CHFCH_3$ | |
| 2.077 | N | $CH_3$ | H | $n-C_3H_7$ | $CHFCH_3$ | |
| 2.078 | N | $-CH_2OCH_2CH_2-$ | | $n-C_3H_7$ | $CHFCH_3$ | |
| 2.079 | N | $-CH=CH-CH=CH-$ | | $n-C_3H_7$ | $CHFCH_3$ | |
| 2.080 | N | $iso-C_3H_7$ | H | $i-C_3H_7$ | $CF_3$ | |
| 2.081 | N | $n-C_4H_9$ | H | $i-C_3H_7$ | $CF_3$ | |
| 2.082 | N | $-(CH_2)_3-$ | | $i-C_3H_7$ | $CHF_2$ | |
| 2.083 | N | $-(CH_2)_4-$ | | $i-C_3H_7$ | $CHF_2$ | |
| 2.084 | N | $-CH_2OCH_2CH_2-$ | | $i-C_3H_7$ | $CH_2F$ | |
| 2.085 | N | $-CH=CH-CH=CH-$ | | $i-C_3H_7$ | $CH_2F$ | |
| 2.086 | N | H | H | $i-C_3H_7$ | $CHFCH_3$ | |
| 2.087 | N | $CH_3$ | H | $i-C_3H_7$ | $CHFCH_3$ | |
| 2.088 | N | $C_2H_5$ | H | $i-C_3H_7$ | $CHFCH_3$ | |
| 2.089 | N | $n-C_3H_7$ | H | $i-C_3H_7$ | $CHFCH_3$ | |
| 2.090 | N | $-(CH_2)_3-$ | | $n-C_4H_9$ | $CF_3$ | |
| 2.091 | N | $-(CH_2)_4-$ | | $n-C_4H_9$ | $CF_3$ | |
| 2.092 | N | $-CH_2OCH_2CH_2-$ | | $n-C_4H_9$ | $CHF_2$ | |
| 2.093 | N | $-CH=CH-CH=CH-$ | | $n-C_4H_9$ | $CHF_2$ | |
| 2.094 | N | $C_2H_5$ | $CH_3$ | $n-C_4H_9$ | $CH_2F$ | |
| 2.095 | CH | H | H | $n-C_4H_9$ | $CH_2F$ | |
| 2.096 | N | H | H | $n-C_4H_9$ | $CHFCH_3$ | |
| 2.097 | N | $CH_3$ | H | $n-C_4H_9$ | $CHFCH_3$ | |

EXAMPLE 7

General process for the preparation of esters of formula Ia (A≠OH)

A 1 to 3 molar amount of an alcohol of formula ROH is added to a solution of a compound of formula Ib in a base, such as triethylamine or pyridine, and the mixture is left at room temperature for from 2 to 3 days. The mixture is then concentrated to dryness and, if necessary, the resulting product is further purified by recrystallisation or chromatography.

The esters of formula Ia is given in Table 3 below can be prepared in accordance with Example 7.

TABLE 3

| Comp. no. | A | X | $R^1$ | $R^2$ | $R^3$ | $R^4$ | m.p. [°C.] phys. data |
|---|---|---|---|---|---|---|---|
| 3.001 | $OCH_3$ | N | H | H | $CH_3$ | $CF_3$ | |
| 3.002 | $OC_2H_5$ | N | $CH_3$ | H | $CH_3$ | $CF_3$ | |
| 3.003 | $OCH_3$ | N | $C_2H_5$ | H | $CH_3$ | $CF_3$ | |
| 3.004 | $OC_2H_5$ | N | $n-C_3H_7$ | H | $CH_3$ | $CF_3$ | |
| 3.005 | $OCH_3$ | N | $iso-C_3H_7$ | H | $CH_3$ | $CF_3$ | |
| 3.006 | $OC_2H_5$ | N | $n-C_4H_9$ | H | $CH_3$ | $CF_3$ | |
| 3.007 | $OCH_3$ | N | $-(CH_2)_3-$ | | $CH_3$ | $CF_3$ | |
| 3.008 | $OC_2H_5$ | N | $-(CH_2)_4-$ | | $CH_3$ | $CF_3$ | |
| 3.009 | $OCH_3$ | N | $-CH_2OCH_2CH_2-$ | | $CH_3$ | $CF_3$ | |
| 3.010 | $OC_2H_5$ | N | $-CH=CH-CH=CH-$ | | $CH_3$ | $CF_3$ | |
| 3.011 | $OC_2H_5$ | N | $C_2H_5$ | $CH_3$ | $CH_3$ | $CF_3$ | |

TABLE 3-continued

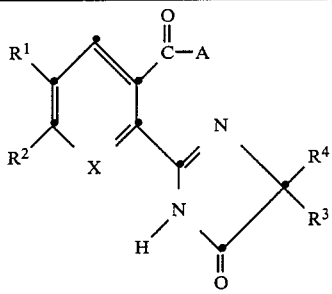

| Comp. no. | A | X | R¹ | R² | R³ | R⁴ | m.p. [°C.] phys. data |
|---|---|---|---|---|---|---|---|
| 3.012 | OCH₃ | CH | H | H | CH₃ | CF₃ | |
| 3.013 | OCH₃ | CH | CH₃ | H | CH₃ | CF₃ | |
| 3.014 | OCH₃ | CH | H | CH₃ | CH₃ | CF₃ | |
| 3.015 | OC₂H₅ | N | H | H | CH₃ | CHF₂ | |
| 3.016 | OCH₃ | N | CH₃ | H | CH₃ | CHF₂ | |
| 3.017 | OC₂H₅ | N | C₂H₅ | H | CH₃ | CHF₂ | |
| 3.018 | OC₂H₅ | N | n-C₃H₇ | H | CH₃ | CHF₂ | |
| 3.019 | OCH₃ | N | iso-C₃H₇ | H | CH₃ | CHF₂ | |
| 3.020 | OC₂H₅ | N | n-C₄H₉ | H | CH₃ | CHF₂ | |
| 3.021 | OC₂H₅ | N | —(CH₂)₃— | | CH₃ | CHF₂ | |
| 3.022 | OCH₃ | N | —(CH₂)₄— | | CH₃ | CHF₂ | |
| 3.023 | OC₂H₅ | N | —CH₂OCH₂CH₂— | | CH₃ | CHF₂ | |
| 3.024 | OCH₃ | N | —CH=CH—CH=CH— | | CH₃ | CHF₂ | |
| 3.025 | OC₂H₅ | N | C₂H₅ | CH₃ | CH₃ | CHF₂ | |
| 3.026 | OCH₃ | CH | H | H | CH₃ | CHF₂ | |
| 3.027 | OC₂H₅ | CH | CH₃ | H | CH₃ | CHF₂ | |
| 3.028 | OCH₃ | CH | H | CH₃ | CH₃ | CHF₂ | |
| 3.029 | OC₂H₅ | N | H | H | CH₃ | CH₂F | |
| 3.030 | OCH₃ | N | CH₃ | H | CH₃ | CH₂F | |
| 3.031 | OC₂H₅ | N | C₂H₅ | H | CH₃ | CH₂F | |
| 3.032 | OCH₃ | N | n-C₃H₇ | H | CH₃ | CH₂F | |
| 3.033 | OC₂H₅ | N | iso-C₃H₇ | H | CH₃ | CH₂F | |
| 3.034 | OCH₃ | N | n-C₄H₉ | H | CH₃ | CH₂F | |
| 3.035 | OC₂H₅ | N | —(CH₂)₃— | | CH₃ | CH₂F | |
| 3.036 | OCH₃ | N | —(CH₂)₄— | | CH₃ | CH₂F | |
| 3.037 | OC₂H₅ | N | —CH₂OCH₂CH₂— | | CH₃ | CH₂F | |
| 3.038 | OCH₃ | N | —CH=CH—CH=CH— | | CH₃ | CH₂F | |
| 3.039 | OC₂H₅ | N | C₂H₅ | CH₃ | CH₃ | CH₂F | |
| 3.040 | OCH₃ | CH | H | H | CH₃ | CH₂F | |
| 3.041 | OC₂H₅ | CH | CH₃ | H | CH₃ | CH₂F | |
| 3.042 | OCH₃ | CH | H | CH₃ | CH₃ | CH₂F | |
| 3.043 | OCH₃ | N | H | H | CH₃ | CHFCH₃ | resin |
| 3.044 | OCH₃ | N | CH₃ | H | CH₃ | CHFCH₃ | |
| 3.045 | OCH₃ | N | C₂H₅ | H | CH₃ | CHFCH₃ | |
| 3.046 | OCH₃ | N | n-C₃H₇ | H | CH₃ | CHFCH₃ | |
| 3.047 | OC₂H₅ | N | iso-C₃H₇ | H | CH₃ | CHFCH₃ | |
| 3.048 | OCH₃ | N | n-C₄H₉ | H | CH₃ | CHFCH₃ | |
| 3.049 | OC₂H₅ | N | —(CH₂)₃— | | CH₃ | CHFCH₃ | |
| 3.050 | OCH₃ | N | —(CH₂)₄— | | CH₃ | CHFCH₃ | |
| 3.051 | OCH₃ | N | —CH₂OCH₂CH₂— | | CH₃ | CHFCH₃ | |
| 3.052 | OCH₃ | N | —CH=CH—CH=CH— | | CH₃ | CHFCH₃ | |
| 3.053 | OC₂H₅ | N | C₂H₅ | CH₃ | CH₃ | CHFCH₃ | |
| 3.054 | OCH₃ | CH | H | H | CH₃ | CHFCH₃ | |
| 3.055 | OC₂H₅ | CH | CH₃ | H | CH₃ | CHFCH₃ | |
| 3.056 | OCH₃ | CH | H | CH₃ | CH₃ | CHFCH₃ | |
| 3.057 | OC₂H₅ | N | H | H | C₂H₅ | CF₃ | |
| 3.058 | OCH₃ | N | CH₃ | H | C₂H₅ | CF₃ | |
| 3.059 | OCH₃ | CH | H | H | C₂H₅ | CF₃ | |
| 3.060 | OCH₃ | N | C₂H₅ | H | C₂H₅ | CHF₂ | |
| 3.061 | OC₂H₅ | N | n-C₃H₇ | H | C₂H₅ | CHF₂ | |
| 3.062 | OC₂H₅ | N | iso-C₃H₇ | H | C₂H₅ | CH₂F | |
| 3.063 | OCH₃ | N | n-C₄H₉ | H | C₂H₅ | CH₂F | |
| 3.064 | OCH₃ | CH | CH₃ | H | C₂H₅ | CH₂F | |
| 3.065 | OCH₃ | N | —(CH₂)₃— | | C₂H₅ | CHFCH₃ | |
| 3.066 | OCH₃ | N | —(CH₂)₄— | | C₂H₅ | CHFCH₃ | |
| 3.067 | OC₂H₅ | N | —CH₂OCH₂CH₂— | | C₂H₅ | CHFCH₃ | |
| 3.068 | OCH₃ | N | —CH=CH—CH=CH— | | C₂H₅ | CHFCH₃ | |
| 3.069 | OCH₃ | CH | H | CH₃ | C₂H₅ | CHFCH₃ | |
| 3.070 | OC₂H₅ | N | C₂H₅ | H | n-C₃H₇ | CF₃ | |
| 3.071 | OCH₃ | N | n-C₃H₇ | H | n-C₃H₇ | CF₃ | |
| 3.072 | OCH₃ | N | iso-C₃H₇ | H | n-C₃H₇ | CHF₂ | |
| 3.073 | OC₂H₅ | N | n-C₄H₉ | H | n-C₃H₇ | CHF₂ | |
| 3.074 | OC₂H₅ | N | —(CH₂)₃— | | n-C₃H₇ | CH₂F | |
| 3.075 | OCH₃ | N | —(CH₂)₄— | | n-C₃H₇ | CH₂F | |
| 3.076 | OCH₃ | N | H | H | n-C₃H₇ | CHFCH₃ | |

TABLE 3-continued

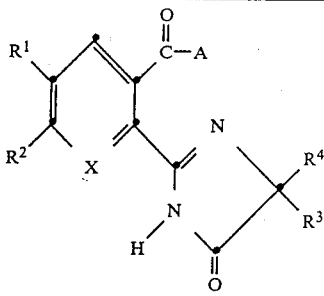

| Comp. no. | A | X | R¹ | R² | R³ | R⁴ | m.p. [°C.] phys. data |
|---|---|---|---|---|---|---|---|
| 3.077 | OC₂H₅ | N | CH₃ | H | n-C₃H₇ | CHFCH₃ | |
| 3.078 | OCH₃ | N | —CH₂OCH₂CH₂— | | n-C₃H₇ | CHFCH₃ | |
| 3.079 | OC₂H₅ | N | —CH=CH—CH=CH— | | n-C₃H₇ | CHFCH₃ | |
| 3.080 | OC₂H₅ | N | iso-C₃H₇ | H | i-C₃H₇ | CF₃ | |
| 3.081 | OCH₃ | N | n-C₄H₉ | H | i-C₃H₇ | CF₃ | |
| 3.082 | OC₂H₅ | N | —(CH₂)₃— | | i-C₃H₇ | CHF₂ | |
| 3.083 | OCH₃ | N | —(CH₂)₄— | | i-C₃H₇ | CHF₂ | |
| 3.084 | OCH₃ | N | —CH₂OCH₂CH₂— | | i-C₃H₇ | CH₂F | |
| 3.085 | OC₂H₅ | N | —CH=CH—CH=CH— | | i-C₃H₇ | CH₂F | |
| 3.086 | OCH₃ | N | H | H | i-C₃H₇ | CHFCH₃ | |
| 3.087 | OCH₃ | N | CH₃ | H | i-C₃H₇ | CHFCH₃ | |
| 3.088 | OC₂H₅ | N | C₂H₅ | H | i-C₃H₇ | CHFCH₃ | |
| 3.089 | OCH₃ | N | n-C₃H₇ | H | i-C₃H₇ | CHFCH₃ | |
| 3.090 | OCH₃ | N | —(CH₂)₃— | | n-C₄H₉ | CF₃ | |
| 3.091 | OC₂H₅ | N | —(CH₂)₄— | | n-C₄H₉ | CF₃ | |
| 3.092 | OCH₃ | N | —CH₂OCH₂CH₂— | | n-C₄H₉ | CHF₂ | |
| 3.093 | OC₂H₅ | N | —CH=CH—CH=CH— | | n-C₄H₉ | CHF₂ | |
| 3.094 | OCH₃ | N | C₂H₅ | CH₃ | n-C₄H₉ | CH₂F | |
| 3.095 | OCH₃ | CH | H | H | n-C₄H₉ | CH₂F | |
| 3.096 | OCH₃ | N | H | H | n-C₄H₉ | CHFCH₃ | |
| 3.097 | OCH₃ | N | CH₃ | H | n-C₄H₉ | CHFCH₃ | |
| 3.098 | O—(n-C₃H₇) | N | H | H | CH₃ | CF₃ | |
| 3.099 | O—(iso-C₃H₇) | N | CH₃ | H | CH₃ | CF₃ | |
| 3.100 | O—(n-C₃H₇) | N | C₂H₅ | H | CH₃ | CF₃ | |
| 3.101 | O—(n-C₃H₇) | N | n-C₃H₇ | H | CH₃ | CF₃ | |
| 3.102 | O—(iso-C₃H₇) | N | iso-C₃H₇ | H | CH₃ | CF₃ | |
| 3.103 | O—(n-C₃H₇) | N | n-C₄H₉ | H | CH₃ | CF₃ | |
| 3.104 | O—(n-C₃H₇) | N | —(CH₂)₃— | | CH₃ | CF₃ | |
| 3.105 | O—(n-C₃H₇) | N | —(CH₂)₄— | | CH₃ | CF₃ | |
| 3.106 | O—(n-C₃H₇) | N | —CH₂OCH₂CH₂— | | CH₃ | CF₃ | |
| 3.107 | O—(iso-C₃H₇) | N | —CH=CH—CH=CH— | | CH₃ | CF₃ | |
| 3.108 | O—(n-C₃H₇) | N | C₂H₅ | CH₃ | CH₃ | CF₃ | |
| 3.109 | O—(n-C₃H₇) | CH | H | H | CH₃ | CF₃ | |
| 3.110 | O—(n-C₃H₇) | CH | CH₃ | H | CH₃ | CF₃ | |
| 3.111 | O—(iso-C₃H₇) | CH | H | CH₃ | CH₃ | CF₃ | |
| 3.112 | O—(n-C₃H₇) | N | H | H | CH₃ | CHF₂ | |
| 3.113 | O—(n-C₃H₇) | N | CH₃ | H | CH₃ | CHF₂ | |
| 3.114 | O—(n-C₃H₇) | N | C₂H₅ | H | CH₃ | CHF₂ | |
| 3.115 | O—(n-C₃H₇) | N | n-C₃H₇ | H | CH₃ | CHF₂ | |
| 3.116 | O—(iso-C₃H₇) | N | iso-C₃H₇ | H | CH₃ | CHF₂ | |
| 3.117 | O—(n-C₃H₇) | N | n-C₄H₉ | H | CH₃ | CHF₂ | |
| 3.118 | O—(n-C₃H₇) | N | —(CH₂)₃— | | CH₃ | CHF₂ | |
| 3.119 | O—(iso-C₃H₇) | N | —(CH₂)₄— | | CH₃ | CHF₂ | |
| 3.120 | O—(n-C₃H₇) | N | —CH₂OCH₂CH₂— | | CH₃ | CHF₂ | |
| 3.121 | O—(n-C₃H₇) | N | —CH=CH—CH=CH— | | CH₃ | CHF₂ | |
| 3.122 | O—(n-C₃H₇) | N | C₂H₅ | CH₃ | CH₃ | CHF₂ | |
| 3.123 | O—(n-C₃H₇) | CH | H | H | CH₃ | CHF₂ | |
| 3.124 | O—(iso-C₃H₇) | CH | CH₃ | H | CH₃ | CHF₂ | |
| 3.125 | O—(n-C₃H₇) | CH | H | CH₃ | CH₃ | CHF₂ | |
| 3.126 | O—(n-C₃H₇) | N | H | H | CH₃ | CH₂F | |
| 3.127 | O—(n-C₃H₇) | N | CH₃ | H | CH₃ | CH₂F | |
| 3.128 | O—(iso-C₃H₇) | N | C₂H₅ | H | CH₃ | CH₂F | |
| 3.129 | O—(n-C₃H₇) | N | n-C₃H₇ | H | CH₃ | CH₂F | |
| 3.130 | O—(n-C₃H₇) | N | iso-C₃H₇ | H | CH₃ | CH₂F | |
| 3.131 | O—(n-C₃H₇) | N | n-C₄H₉ | H | CH₃ | CH₂F | |
| 3.132 | O—(iso-C₃H₇) | N | —(CH₂)₃— | | CH₃ | CH₂F | |
| 3.133 | O—(n-C₃H₇) | N | —(CH₂)₄— | | CH₃ | CH₂F | |
| 3.134 | O—(n-C₃H₇) | N | —CH₂OCH₂CH₂— | | CH₃ | CH₂F | |
| 3.135 | O—(n-C₃H₇) | N | —CH=CH—CH=CH— | | CH₃ | CH₂F | |
| 3.136 | O—(n-C₃H₇) | N | C₂H₅ | CH₃ | CH₃ | CH₂F | |
| 3.137 | O—(iso-C₃H₇) | CH | H | H | CH₃ | CH₂F | |
| 3.138 | O—(n-C₃H₇) | CH | CH₃ | H | CH₃ | CH₂F | |
| 3.139 | O—(n-C₃H₇) | CH | H | CH₃ | CH₃ | CH₂F | |
| 3.140 | O—(n-C₃H₇) | N | H | H | CH₃ | CHFCH₃ | |
| 3.141 | O—(iso-C₃H₇) | N | CH₃ | H | CH₃ | CHFCH₃ | |

TABLE 3-continued

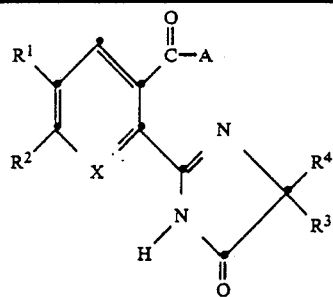

| Comp. no. | A | X | R¹ | R² | R³ | R⁴ | m.p. [°C.] phys. data |
|---|---|---|---|---|---|---|---|
| 3.142 | O—(n-C$_3$H$_7$) | N | C$_2$H$_5$ | H | CH$_3$ | CHFCH$_3$ | |
| 3.143 | O—(n-C$_3$H$_7$) | N | n-C$_3$H$_7$ | H | CH$_3$ | CHFCH$_3$ | |
| 3.144 | O—(iso-C$_3$H$_7$) | N | iso-C$_3$H$_7$ | H | CH$_3$ | CHFCH$_3$ | |
| 3.145 | O—(n-C$_3$H$_7$) | N | n-C$_4$H$_9$ | H | CH$_3$ | CHFCH$_3$ | |
| 3.146 | O—(n-C$_3$H$_7$) | N | —(CH$_2$)$_3$— | | CH$_3$ | CHFCH$_3$ | |
| 3.147 | O—(iso-C$_3$H$_7$) | N | —(CH$_2$)$_4$— | | CH$_3$ | CHFCH$_3$ | |
| 3.148 | O—(n-C$_3$H$_7$) | N | —CH$_2$OCH$_2$CH$_2$— | | CH$_3$ | CHFCH$_3$ | |
| 3.149 | O—(n-C$_3$H$_7$) | N | —CH=CH—CH=CH— | | CH$_3$ | CHFCH$_3$ | |
| 3.150 | O—(iso-C$_3$H$_7$) | N | C$_2$H$_5$ | CH$_3$ | CH$_3$ | CHFCH$_3$ | |
| 3.151 | O—(n-C$_3$H$_7$) | CH | H | H | CH$_3$ | CHFCH$_3$ | |
| 3.152 | O—(n-C$_3$H$_7$) | CH | CH$_3$ | H | CH$_3$ | CHFCH$_3$ | |
| 3.153 | O—(n-C$_3$H$_7$) | CH | H | CH$_3$ | CH$_3$ | CHFCH$_3$ | |
| 3.154 | O—(iso-C$_3$H$_7$) | N | H | H | C$_2$H$_5$ | CF$_3$ | |
| 3.155 | O—(n-C$_3$H$_7$) | N | CH$_3$ | H | C$_2$H$_5$ | CF$_3$ | |
| 3.156 | O—(n-C$_3$H$_7$) | CH | H | H | C$_2$H$_5$ | CF$_3$ | |
| 3.157 | O—(n-C$_3$H$_7$) | N | C$_2$H$_5$ | H | C$_2$H$_5$ | CHF$_2$ | |
| 3.158 | O—(iso-C$_3$H$_7$) | N | n-C$_3$H$_7$ | H | C$_2$H$_5$ | CHF$_2$ | |
| 3.159 | O—(iso-C$_3$H$_7$) | N | iso-C$_3$H$_7$ | H | C$_2$H$_5$ | CH$_2$F | |
| 3.160 | O—(n-C$_3$H$_7$) | N | n-C$_4$H$_9$ | H | C$_2$H$_5$ | CH$_2$F | |
| 3.161 | O—(n-C$_3$H$_7$) | CH | CH$_3$ | H | C$_2$H$_5$ | CH$_2$F | |
| 3.162 | O—(n-C$_3$H$_7$) | N | —(CH$_2$)$_3$— | | C$_2$H$_5$ | CHFCH$_3$ | |
| 3.163 | O—(iso-C$_3$H$_7$) | N | —(CH$_2$)$_4$— | | C$_2$H$_5$ | CHFCH$_3$ | |
| 3.164 | O—(n-C$_3$H$_7$) | N | —CH$_2$OCH$_2$CH$_2$— | | C$_2$H$_5$ | CHFCH$_3$ | |
| 3.165 | O—(iso-C$_3$H$_7$) | N | —CH=CH—CH=CH— | | C$_2$H$_5$ | CHFCH$_3$ | |
| 3.166 | O—(n-C$_3$H$_7$) | CH | H | CH$_3$ | C$_2$H$_5$ | CHFCH$_3$ | |
| 3.167 | O—(iso-C$_3$H$_7$) | N | C$_2$H$_5$ | H | n-C$_3$H$_7$ | CF$_3$ | |
| 3.168 | O—(n-C$_3$H$_7$) | N | n-C$_3$H$_7$ | H | n-C$_3$H$_7$ | CF$_3$ | |
| 3.169 | O—(iso-C$_3$H$_7$) | N | iso-C$_3$H$_7$ | H | n-C$_3$H$_7$ | CHF$_2$ | |
| 3.170 | O—(n-C$_3$H$_7$) | N | n-C$_4$H$_9$ | H | n-C$_3$H$_7$ | CHF$_2$ | |
| 3.171 | O—(iso-C$_3$H$_7$) | N | —(CH$_2$)$_3$— | | n-C$_3$H$_7$ | CH$_2$F | |
| 3.172 | O—(n-C$_3$H$_7$) | N | —(CH$_2$)$_4$— | | n-C$_3$H$_7$ | CH$_2$F | |
| 3.173 | O—(n-C$_3$H$_7$) | N | H | H | n-C$_3$H$_7$ | CHFCH$_3$ | |
| 3.174 | O—(iso-C$_3$H$_7$) | N | CH$_3$ | H | n-C$_3$H$_7$ | CHFCH$_3$ | |
| 3.175 | O—(iso-C$_3$H$_7$) | N | —CH$_2$OCH$_2$CH$_2$— | | n-C$_3$H$_7$ | CHFCH$_3$ | |
| 3.176 | O—(n-C$_3$H$_7$) | N | —CH=CH—CH=CH— | | n-C$_3$H$_7$ | CHFCH$_3$ | |
| 3.177 | O—(n-C$_3$H$_7$) | N | iso-C$_3$H$_7$ | H | i-C$_3$H$_7$ | CF$_3$ | |
| 3.178 | O—(iso-C$_3$H$_7$) | N | n-C$_4$H$_9$ | H | i-C$_3$H$_7$ | CF$_3$ | |
| 3.179 | O—(iso-C$_3$H$_7$) | N | —(CH$_2$)$_3$— | | i-C$_3$H$_7$ | CHF$_2$ | |
| 3.180 | O—(n-C$_3$H$_7$) | N | —(CH$_2$)$_4$— | | i-C$_3$H$_7$ | CHF$_2$ | |
| 3.181 | O—(iso-C$_3$H$_7$) | N | —CH$_2$OCH$_2$CH$_2$— | | i-C$_3$H$_7$ | CH$_2$F | |
| 3.182 | O—(n-C$_3$H$_7$) | N | —CH=CH—CH=CH— | | i-C$_3$H$_7$ | CH$_2$F | |
| 3.183 | O—(n-C$_3$H$_7$) | N | H | H | i-C$_3$H$_7$ | CHFCH$_3$ | |
| 3.184 | O—(iso-C$_3$H$_7$) | N | CH$_3$ | H | i-C$_3$H$_7$ | CHFCH$_3$ | |
| 3.185 | O—(n-C$_3$H$_7$) | N | C$_2$H$_5$ | H | i-C$_3$H$_7$ | CHFCH$_3$ | |
| 3.186 | O—(iso-C$_3$H$_7$) | N | n-C$_3$H$_7$ | H | i-C$_3$H$_7$ | CHFCH$_3$ | |
| 3.187 | O—(iso-C$_3$H$_7$) | N | —(CH$_2$)$_3$— | | n-C$_4$H$_9$ | CF$_3$ | |
| 3.188 | O—(n-C$_3$H$_7$) | N | —(CH$_2$)$_4$— | | n-C$_4$H$_9$ | CF$_3$ | |
| 3.189 | O—(n-C$_3$H$_7$) | N | —CH$_2$OCH$_2$CH$_2$— | | n-C$_4$H$_9$ | CHF$_2$ | |
| 3.190 | O—(iso-C$_3$H$_7$) | N | —CH=CH—CH=CH— | | n-C$_4$H$_9$ | CHF$_2$ | |
| 3.191 | O—(iso-C$_3$H$_7$) | N | C$_2$H$_5$ | CH$_3$ | n-C$_4$H$_9$ | CH$_2$F | |
| 3.192 | O—(n-C$_3$H$_7$) | CH | H | H | n-C$_4$H$_9$ | CH$_2$F | |
| 3.193 | O—(n-C$_3$H$_7$) | N | H | H | n-C$_4$H$_9$ | CHFCH$_3$ | |
| 3.194 | O—(iso-C$_3$H$_7$) | N | CH$_3$ | H | n-C$_4$H$_9$ | CHFCH$_3$ | |
| 3.195 | O—(n-C$_4$H$_9$) | N | H | H | CH$_3$ | CF$_3$ | |
| 3.196 | O—(n-C$_4$H$_9$) | N | CH$_3$ | H | CH$_3$ | CF$_3$ | |
| 3.197 | O—(sek.-C$_4$H$_9$) | N | C$_2$H$_5$ | H | CH$_3$ | CF$_3$ | |
| 3.198 | O—(n-C$_4$H$_9$) | N | n-C$_3$H$_7$ | H | CH$_3$ | CF$_3$ | |
| 3.199 | O—(sek.-C$_4$H$_9$) | N | iso-C$_3$H$_7$ | H | CH$_3$ | CF$_3$ | |
| 3.200 | O—(n-C$_4$H$_9$) | N | n-C$_4$H$_9$ | H | CH$_3$ | CF$_3$ | |
| 3.201 | O—(iso-C$_4$H$_9$) | N | —(CH$_2$)$_3$— | | CH$_3$ | CF$_3$ | |
| 3.202 | O—(n-C$_4$H$_9$) | N | —(CH$_2$)$_4$— | | CH$_3$ | CF$_3$ | |
| 3.203 | O—(tert-C$_4$H$_9$) | N | —CH$_2$OCH$_2$CH$_2$— | | CH$_3$ | CF$_3$ | |
| 3.204 | O—(n-C$_4$H$_9$) | N | —CH=CH—CH=CH— | | CH$_3$ | CF$_3$ | |
| 3.205 | O—(n-C$_4$H$_9$) | N | C$_2$H$_5$ | CH$_3$ | CH$_3$ | CF$_3$ | |
| 3.206 | O—(n-C$_4$H$_9$) | CH | H | H | CH$_3$ | CF$_3$ | |

TABLE 3-continued

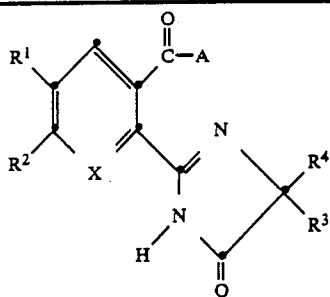

| Comp. no. | A | X | R¹ | R² | R³ | R⁴ | m.p. [°C.] phys. data |
|---|---|---|---|---|---|---|---|
| 3.207 | O—(sek.-C₄H₉) | CH | CH₃ | H | CH₃ | CF₃ | |
| 3.208 | O—(n-C₄H₉) | CH | H | CH₃ | CH₃ | CF₃ | |
| 3.209 | O—(iso-C₄H₉) | N | H | H | CH₃ | CHF₂ | |
| 3.210 | O—(n-C₄H₉) | N | CH₃ | H | CH₃ | CHF₂ | |
| 3.211 | O—(n-C₄H₉) | N | C₂H₅ | H | CH₃ | CHF₂ | |
| 3.212 | O—(tert-C₄H₉) | N | n-C₃H₇ | H | CH₃ | CHF₂ | |
| 3.213 | O—(n-C₄H₉) | N | iso-C₃H₇ | H | CH₃ | CHF₂ | |
| 3.214 | O—(n-C₄H₉) | N | n-C₄H₉ | H | CH₃ | CHF₂ | |
| 3.215 | O—(n-C₄H₉) | N | —(CH₂)₃— | | CH₃ | CHF₂ | |
| 3.216 | O—(iso-C₄H₉) | N | —(CH₂)₄— | | CH₃ | CHF₂ | |
| 3.217 | O—(n-C₄H₉) | N | —CH₂OCH₂CH₂— | | CH₃ | CHF₂ | |
| 3.218 | O—(n-C₄H₉) | N | —CH=CH—CH=CH— | | CH₃ | CHF₂ | |
| 3.219 | O—(tert-C₄H₉) | N | C₂H₅ | CH₃ | CH₃ | CHF₂ | |
| 3.220 | O—(sek.-C₄H₉) | CH | H | H | CH₃ | CHF₂ | |
| 3.221 | O—(sek.-C₄H₉) | CH | CH₃ | H | CH₃ | CHF₂ | |
| 3.222 | O—(n-C₄H₉) | CH | H | CH₃ | CH₃ | CHF₂ | |
| 3.223 | O—(n-C₄H₉) | N | H | H | CH₃ | CH₂F | |
| 3.224 | O—(n-C₄H₉) | N | CH₃ | H | CH₃ | CH₂F | |
| 3.225 | O—(iso-C₄H₉) | N | C₂H₅ | H | CH₃ | CH₂F | |
| 3.226 | O—(sek.-C₄H₉) | N | n-C₃H₇ | H | CH₃ | CH₂F | |
| 3.227 | O—(n-C₄H₉) | N | iso-C₃H₇ | H | CH₃ | CH₂F | |
| 3.228 | O—(tert-C₄H₉) | N | n-C₄H₉ | H | CH₃ | CH₂F | |
| 3.229 | O—(n-C₄H₉) | N | —(CH₂)₃— | | CH₃ | CH₂F | |
| 3.230 | O—(n-C₄H₉) | N | —(CH₂)₄— | | CH₃ | CH₂F | |
| 3.231 | O—(tert-C₄H₉) | N | —CH₂OCH₂CH₂— | | CH₃ | CH₂F | |
| 3.232 | O—(iso-C₄H₉) | N | —CH=CH—CH=CH— | | CH₃ | CH₂F | |
| 3.233 | O—(sek.-C₄H₉) | N | C₂H₅ | CH₃ | CH₃ | CH₂F | |
| 3.234 | O—(n-C₄H₉) | CH | H | H | CH₃ | CH₂F | |
| 3.235 | O—(n-C₄H₉) | CH | CH₃ | H | CH₃ | CH₂F | |
| 3.236 | O—(n-C₄H₉) | CH | H | CH₃ | CH₃ | CH₂F | |
| 3.237 | O—(n-C₄H₉) | N | H | H | CH₃ | CHFCH₃ | |
| 3.238 | O—(tert-C₄H₉) | N | CH₃ | H | CH₃ | CHFCH₃ | |
| 3.239 | O—(iso-C₄H₉) | N | C₂H₅ | H | CH₃ | CHFCH₃ | |
| 3.240 | O—(sek.-C₄H₉) | N | n-C₃H₇ | H | CH₃ | CHFCH₃ | |
| 3.241 | O—(n-C₄H₉) | N | iso-C₃H₇ | H | CH₃ | CHFCH₃ | |
| 3.242 | O—(n-C₄H₉) | N | n-C₄H₉ | H | CH₃ | CHFCH₃ | |
| 3.243 | O—(sek.-C₄H₉) | N | —(CH₂)₃— | | CH₃ | CHFCH₃ | |
| 3.244 | O—(iso-C₄H₉) | N | —(CH₂)₄— | | CH₃ | CHFCH₃ | |
| 3.245 | O—(n-C₄H₉) | N | —CH₂OCH₂CH₂— | | CH₃ | CHFCH₃ | |
| 3.246 | O—(n-C₄H₉) | N | —CH=CH—CH=CH— | | CH₃ | CHFCH₃ | |
| 3.247 | O—(sek.-C₄H₉) | N | C₂H₅ | CH₃ | CH₃ | CHFCH₃ | |
| 3.248 | O—(iso-C₄H₉) | CH | H | H | CH₃ | CHFCH₃ | |
| 3.249 | O—(n-C₄H₉) | CH | CH₃ | H | CH₃ | CHFCH₃ | |
| 3.250 | O—(n-C₄H₉) | CH | H | CH₃ | CH₃ | CHFCH₃ | |
| 3.251 | O—(n-C₄H₉) | N | H | H | C₂H₅ | CF₃ | |
| 3.252 | O—(tert-C₄H₉) | N | CH₃ | H | C₂H₅ | CF₃ | |
| 3.253 | O—(n-C₄H₉) | CH | H | H | C₂H₅ | CF₃ | |
| 3.254 | O—(n-C₄H₉) | N | C₂H₅ | H | C₂H₅ | CHF₂ | |
| 3.255 | O—(sek.-C₄H₉) | N | n-C₃H₇ | H | C₂H₅ | CHF₂ | |
| 3.256 | O—(n-C₄H₉) | N | iso-C₃H₇ | H | C₂H₅ | CH₂F | |
| 3.257 | O—(n-C₄H₉) | N | n-C₄H₉ | H | C₂H₅ | CH₂F | |
| 3.258 | O—(sek.-C₄H₉) | CH | CH₃ | H | C₂H₅ | CH₂F | |
| 3.259 | O—(n-C₄H₉) | N | —(CH₂)₃— | | C₂H₅ | CHFCH₃ | |
| 3.260 | O—(tert-C₄H₉) | N | —(CH₂)₄— | | C₂H₅ | CHFCH₃ | |
| 3.261 | O—(iso-C₄H₉) | N | —CH₂OCH₂CH₂— | | C₂H₅ | CHFCH₃ | |
| 3.262 | O—(n-C₄H₉) | N | —CH=CH—CH=CH— | | C₂H₅ | CHFCH₃ | |
| 3.263 | O—(n-C₄H₉) | CH | H | CH₃ | C₂H₅ | CHFCH₃ | |
| 3.264 | O—(n-C₄H₉) | N | C₂H₅ | H | n-C₃H₇ | CF₃ | |
| 3.265 | O—(n-C₄H₉) | N | n-C₃H₇ | H | n-C₃H₇ | CF₃ | |
| 3.266 | O—(sek.-C₄H₉) | N | iso-C₃H₇ | H | n-C₃H₇ | CHF₂ | |
| 3.267 | O—(n-C₄H₉) | N | n-C₄H₉ | H | n-C₃H₇ | CHF₂ | |
| 3.268 | O—(n-C₄H₉) | N | —(CH₂)₃— | | n-C₃H₇ | CH₂F | |
| 3.269 | O—(n-C₄H₉) | N | —(CH₂)₄— | | n-C₃H₇ | CH₂F | |
| 3.270 | O—(sek.-C₄H₉) | N | H | H | n-C₃H₇ | CHFCH₃ | |
| 3.271 | O—(n-C₄H₉) | N | CH₃ | H | n-C₃H₇ | CHFCH₃ | |

TABLE 3-continued

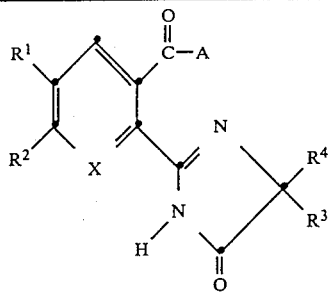

| Comp. no. | A | X | R¹ | R² | R³ | R⁴ | m.p. [°C.] phys. data |
|---|---|---|---|---|---|---|---|
| 3.272 | O—(iso-C₄H₉) | N | —CH₂OCH₂CH₂— | | n-C₃H₇ | CHFCH₃ | |
| 3.273 | O—(n-C₄H₉) | N | —CH=CH—CH=CH— | | n-C₃H₇ | CHFCH₃ | |
| 3.274 | O—(n-C₄H₉) | N | iso-C₃H₇ | H | i-C₃H₇ | CF₃ | |
| 3.275 | O—(n-C₄H₉) | N | n-C₄H₉) | H | i-C₃H₇ | CF₃ | |
| 3.276 | O—(sek.-C₄H₉) | N | —(CH₂)₃— | | i-C₃H₇ | CHF₂ | |
| 3.277 | O—(n-C₄H₉) | N | —(CH₂)₄— | | i-C₃H₇ | CHF₂ | |
| 3.278 | O—(n-C₄H₉) | N | —CH₂OCH₂CH₂— | | i-C₃H₇ | CH₂F | |
| 3.279 | O—(n-C₄H₉) | N | —CH=CH—CH=CH— | | i-C₃H₇ | CH₂F | |
| 3.280 | O—(n-C₄H₉) | N | H | H | i-C₃H₇ | CHFCH₃ | |
| 3.281 | O—(sek.-C₄H₉) | N | CH₃ | H | i-C₃H₇ | CHFCH₃ | |
| 3.282 | O—(iso-C₄H₉) | N | C₂H₅ | H | i-C₃H₇ | CHFCH₃ | |
| 3.283 | O—(tert-C₄H₉) | N | n-C₃H₇ | H | i-C₃H₇ | CHFCH₃ | |
| 3.284 | O—(n-C₄H₉) | N | —(CH₂)₃— | | n-C₄H₉ | CF₃ | |
| 3.285 | O—(n-C₄H₉) | N | —(CH₂)₄— | | n-C₄H₉ | CF₃ | |
| 3.286 | O—(n-C₄H₉) | N | —CH₂OCH₂CH₂— | | n-C₄H₉ | CHF₂ | |
| 3.287 | O—(sek.-C₄H₉) | N | —CH=CH—CH=CH— | | n-C₄H₉ | CHF₂ | |
| 3.288 | O—(n-C₄H₉) | N | C₂H₅ | CH₃ | n-C₄H₉ | CH₂F | |
| 3.289 | O—(sek-C₄H₉) | CH | H | H | n-C₄H₉ | CH₂F | |
| 3.290 | O—(iso-C₄H₉) | N | H | H | n-C₄H₉ | CHFCH₃ | |
| 3.291 | O—(n-C₄H₉) | N | CH₃ | H | n-C₄H₉ | CHFCH₃ | |
| 3.292 | O—C₂H₅ | N | C₂H₅ | H | CH₃ | CHFCH₃ | 108–110 |
| 3.293 | O—C₂H₅ | N | H | H | CH₃ | CHFCH₃ | 108–110 |

EXAMPLE 8

General process for the preparation of compounds of formula Ic

A solution of an imide of formula III (which can be prepared in accordance with EP-A-0041632, EP-A-0212200, DE-A-3420271 or GB-A-2174395) in toluene is heated to boiling on a water separator in the presence of a 1 to 5 molar amount of powdered NaOH. After cooling, the reaction mixture is filtered over silica gel and washed with ethyl acetate, and the combined filtrates are concentrated to dryness. The product of formula Ic so obtained is, if necessary, recrystallised from a suitable solvent for purification.

The compounds of formula Ic given in Table 4 below can be prepared in accordance with Example 8.

TABLE 4

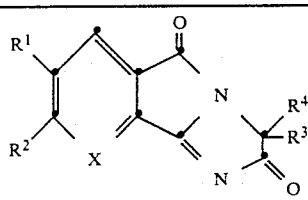

Ic

| Comp. no. | X | R¹ | R² | R³ | R⁴ | m.p. [°C.] phys. data |
|---|---|---|---|---|---|---|
| 4.001 | N | H | H | CH₃ | CF₃ | |
| 4.002 | N | CH₃ | H | CH₃ | CF₃ | |
| 4.003 | N | C₂H₅ | H | CH₃ | CF₃ | |
| 4.004 | N | n-C₃H₇ | H | CH₃ | CF₃ | |
| 4.005 | N | iso-C₃H₇ | H | CH₃ | CF₃ | |
| 4.006 | N | n-C₄H₉ | H | CH₃ | CF₃ | |
| 4.007 | N | —(CH₂)₃— | | CH₃ | CF₃ | |
| 4.008 | N | —(CH₂)₄— | | CH₃ | CF₃ | |
| 4.009 | N | —CH₂OCH₂CH₂— | | CH₃ | CF₃ | |
| 4.010 | N | —CH=CH—CH=CH— | | CH₃ | CF₃ | |
| 4.011 | N | C₂H₅ | CH₃ | CH₃ | CF₃ | |
| 4.012 | CH | H | H | CH₃ | CF₃ | |
| 4.013 | CH | CH₃ | H | CH₃ | CF₃ | |
| 4.014 | CH | H | CH₃ | CH₃ | CF₃ | |
| 4.015 | N | H | H | CH₃ | CHF₂ | |
| 4.016 | N | CH₃ | H | CH₃ | CHF₂ | |

TABLE 4-continued

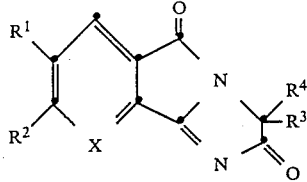

Ic

| Comp. no. | X | R¹ | R² | R³ | R⁴ | m.p. [°C.] phys. data |
|---|---|---|---|---|---|---|
| 4.017 | N | C₂H₅ | H | CH₃ | CHF₂ | |
| 4.018 | N | n-C₃H₇ | H | CH₃ | CHF₂ | |
| 4.019 | N | iso-C₃H₇ | H | CH₃ | CHF₂ | |
| 4.020 | N | n-C₄H₉ | H | CH₃ | CHF₂ | |
| 4.021 | N | —(CH₂)₃— | | CH₃ | CHF₂ | |
| 4.022 | N | —(CH₂)₄— | | CH₃ | CHF₂ | |
| 4.023 | N | —CH₂OCH₂CH₂— | | CH₃ | CHF₂ | |
| 4.024 | N | —CH=CH—CH=CH— | | CH₃ | CHF₂ | |
| 4.025 | N | C₂H₅ | CH₃ | CH₃ | CHF₂ | |
| 4.026 | CH | H | H | CH₃ | CHF₂ | |
| 4.027 | CH | CH₃ | H | CH₃ | CHF₂ | |
| 4.028 | CH | H | CH₃ | CH₃ | CHF₂ | |
| 4.029 | N | H | H | CH₃ | CH₂F | |
| 4.030 | N | CH₃ | H | CH₃ | CH₂F | |
| 4.031 | N | C₂H₅ | H | CH₃ | CH₂F | |
| 4.032 | N | n-C₃H₇ | H | CH₃ | CH₂F | |
| 4.033 | N | iso-C₃H₇ | H | CH₃ | CH₂F | |
| 4.034 | N | n-C₄H₉ | H | CH₃ | CH₂F | |
| 4.035 | N | —(CH₂)₃— | | CH₃ | CH₂F | |
| 4.036 | N | —(CH₂)₄— | | CH₃ | CH₂F | |
| 4.037 | N | —CH₂OCH₂CH₂— | | CH₃ | CH₂F | |
| 4.038 | N | —CH=CH—CH=CH— | | CH₃ | CH₂F | |
| 4.039 | N | C₂H₅ | CH₃ | CH₃ | CH₂F | |
| 4.040 | CH | H | H | CH₃ | CH₂F | |
| 4.041 | CH | CH₃ | H | CH₃ | CH₂F | |
| 4.042 | CH | H | CH₃ | CH₃ | CH₂F | |
| 4.043 | N | H | H | CH₃ | CHFCH₃ | |
| 4.044 | N | CH₃ | H | CH₃ | CHFCH₃ | |
| 4.045 | N | C₂H₅ | H | CH₃ | CHFCH₃ | |
| 4.046 | N | n-C₃H₇ | H | CH₃ | CHFCH₃ | |
| 4.047 | N | iso-C₃H₇ | H | CH₃ | CHFCH₃ | |
| 4.048 | N | n-C₄H₉ | H | CH₃ | CHFCH₃ | |
| 4.049 | N | —(CH₂)₃— | | CH₃ | CHFCH₃ | |
| 4.050 | N | —(CH₂)₄— | | CH₃ | CHFCH₃ | |
| 4.051 | N | —CH₂OCH₂CH₂— | | CH₃ | CHFCH₃ | |
| 4.052 | N | —CH=CH—CH=CH— | | CH₃ | CHFCH₃ | |
| 4.053 | N | C₂H₅ | CH₃ | CH₃ | CHFCH₃ | |
| 4.054 | CH | H | H | CH₃ | CHFCH₃ | |
| 4.055 | CH | CH₃ | H | CH₃ | CHFCH₃ | |
| 4.056 | CH | H | CH₃ | CH₃ | CHFCH₃ | |
| 4.057 | N | H | H | C₂H₅ | CF₃ | |
| 4.058 | N | CH₃ | H | C₂H₅ | CF₃ | |
| 4.059 | CH | H | H | C₂H₅ | CF₃ | |
| 4.060 | N | C₂H₅ | H | C₂H₅ | CHF₂ | |
| 4.061 | N | n-C₃H₇ | H | C₂H₅ | CHF₂ | |
| 4.062 | N | iso-C₃H₇ | H | C₂H₅ | CH₂F | |
| 4.063 | N | n-C₄H₉ | H | C₂H₅ | CH₂F | |
| 4.064 | CH | CH₃ | H | C₂H₅ | CH₂F | |
| 4.065 | N | —(CH₂)₃— | | C₂H₅ | CHFCH₃ | |
| 4.066 | N | —(CH₂)₄— | | C₂H₅ | CHFCH₃ | |
| 4.067 | N | —CH₂OCH₂CH₂— | | C₂H₅ | CHFCH₃ | |
| 4.068 | N | —CH=CH—CH=CH— | | C₂H₅ | CHFCH₃ | |
| 4.069 | CH | H | CH₃ | C₂H₅ | CHFCH₃ | |
| 4.070 | N | C₂H₅ | H | n-C₃H₇ | CF₃ | |
| 4.071 | N | n-C₃H₇ | H | n-C₃H₇ | CF₃ | |
| 4.072 | N | iso-C₃H₇ | H | n-C₃H₇ | CHF₂ | |
| 4.073 | N | n-C₄H₉ | H | n-C₃H₇ | CHF₂ | |
| 4.074 | N | —(CH₂)₃— | | n-C₃H₇ | CH₂F | |
| 4.075 | N | —(CH₂)₄— | | n-C₃H₇ | CH₂F | |
| 4.076 | N | H | H | n-C₃H₇ | CHFCH₃ | |
| 4.077 | N | CH₃ | H | n-C₃H₇ | CHFCH₃ | |
| 4.078 | N | —CH₂OCH₂CH₂— | | n-C₃H₇ | CHFCH₃ | |
| 4.079 | N | —CH=CH—CH=CH— | | n-C₃H₇ | CHFCH₃ | |
| 4.080 | N | iso-C₃H₇ | H | i-C₃H₇ | CF₃ | |
| 4.081 | N | n-C₄H₉ | H | i-C₃H₇ | CF₃ | |
| 4.082 | N | —(CH₂)₃— | | i-C₃H₇ | CHF₂ | |
| 4.083 | N | —(CH₂)₄— | | i-C₃H₇ | CHF₂ | |
| 4.084 | N | —CH₂OCH₂CH₂— | | i-C₃H₇ | CH₂F | |
| 4.085 | N | —CH=CH—CH=CH— | | i-C₃H₇ | CH₂F | |
| 4.086 | N | H | H | i-C₃H₇ | CHFCH₃ | |

TABLE 4-continued $$\text{Structure Ic: } R^1, R^2, X, \text{ with carbonyl group, N-R^4/R^3, etc.}$$

| Comp. no. | X | R¹ | R² | R³ | R⁴ | m.p. [°C.] phys. data |
|---|---|---|---|---|---|---|
| 4.087 | N | CH₃ | H | i-C₃H₇ | CHFCH₃ | |
| 4.088 | N | C₂H₅ | H | i-C₃H₇ | CHFCH₃ | |
| 4.089 | N | n-C₃H₇ | H | i-C₃H₇ | CHFCH₃ | |
| 4.090 | N | —(CH₂)₃— | | n-C₄H₉ | CF₃ | |
| 4.091 | N | —(CH₂)₄— | | n-C₄H₉ | CF₃ | |
| 4.092 | N | —CH₂OCH₂CH₂— | | n-C₄H₉ | CHF₂ | |
| 4.093 | N | —CH=CH—CH=CH— | | n-C₄H₉ | CHF₂ | |
| 4.094 | N | C₂H₅ | CH₃ | n-C₄H₉ | CH₂F | |
| 4.095 | CH | H | H | n-C₄H₉ | CH₂F | |
| 4.096 | N | H | H | n-C₄H₉ | CHFCH₃ | |
| 4.097 | N | CH₃ | H | n-C₄H₉ | CHFCH₃ | |

EXAMPLE 9

Formulation Examples for active ingredients of formula I (throughout, percentages are by weight)

| (a) Wettable powders | (a) | (b) | (c) |
|---|---|---|---|
| a compound of Table 1, 2, 3 or 4 | 20% | 60% | 0.5% |
| sodium lignosulphonate | 5% | 5% | 5% |
| sodium laurylsulphate | 3% | — | — |
| sodium diisobutylnaphthalene-sulphonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| a compound of Table 1, 2, 3 or 4 | 10% | 1% |
| octylphenol polyethylene glycol ether (4-5 moles of ethylene oxide) | 3% | 3% |
| calcium dodecylbenzenesulphonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| a compound of Table 1, 2, 3 or 4 | 0.1% | 1% |
| talcum | 99.9% | — |
| kaolin | — | 99% |

Ready-for-use dusts are obtained by mixing the active ingredient with the carrier and grinding the mixture in a suitable mill.

| (d) Extruder granulate | (a) | (b) |
|---|---|---|
| a compound of Table 1, 2, 3 or 4 | 10% | 1% |
| sodium lignosulphonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| a compound of Table 1, 2, 3 or 4 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| a compound of Table 1, 2, 3 or 4 | 40% | 5% |
| ethylene glycol | 10% | 10% |
| nonylphenol polyethylene glycol ether (15 moles of ethylene oxide) | 6% | 1% |
| sodium lignosulphonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

BIOLOGICAL EXAMPLES

EXAMPLE 10

Pre-emergence herbicidal action

In a greenhouse, immediately after the test plants have been sown in seed trays, the surface of the soil is treated with an aqueous dispersion of the active ingredients obtained from a 25% emulsifiable concentrate. Concentrations of 4 kg of active ingredient/hectare are used. The seed trays are kept in a greenhouse at 22°–25° C. and 50–70% relative humidity, and the test is evaluated 3 weeks later, and the results are assessed in accordance with the following rating.

1 plant has not emerged or has wilted
2–3 very sever damage
4 severe damage
5 moderate damage, the plants are stunted
6 damage, the plant is able to regenerate
7–8 slight damage
9 normal growth, as that of untreated plants.

The compounds of Tables 1 to 4 exhibited pronounced herbicidal action in this test.

EXAMPLE 11

Post-emergence herbicidal action (contact herbicide)

A number of weeds, both mono- and dicotyledonous, are sprayed post-emergence (in the 4- to 6-leaf stage) with an aqueous active ingredient dispersion at a rate of 4 kg of test compound per hectare and kept at 24°–26° C. and 45–60% relative humidity. The test is evaluated 15 days after the treatment in accordance with the rating indicated above. In this test too, the compounds of Tables 1 to 4 exhibit pronounced to very pronounced herbicidal action.

EXAMPLE 12

Pre-emergence herbicidal action

Plastic pots are filled with expanded vermiculite (density: 0.135 g/cm$^3$; water-absorbing capacity: 0.565 1/1). After the non-absorptive vermiculite has been saturated with an aqueous emulsion in deionised water which contains the test compound in a concentration of 70.8 ppm, seeds of the following plants are sown on the surface: cress, Agrostis tenuis, Stellaria media and Digitaria sanguinalis. The pots are then kept in a climatic chamber at 20° C., an illumination of about 20 klux and a relative humidity of 70%. During the germinating phase of 4 to 6 days, the pots are covered with light-permeable material and watered with deionised water to increase the local humidity. After the 5th day, 0.5% of a commercial liquid fertilizer (Greenzit ®) is added to the water. The test is evaluated 12 days after sowing and the action on the test plants is assessed in accordance with the scale given in Example 10.

The results are summarised in Table 5:

TABLE 5

| Compound no. | Kresse | Agrostis | Stellaria | Digitaria |
|---|---|---|---|---|
| 1.043 | 2 | 2 | 2 | 2 |
| 1.044 | 2 | 2 | 2 | 2 |
| 1.045 | 2 | 2 | 2 | 2 |
| 1.098 | 2 | 2 | 2 | 2 |

I claim:

1. A compound of formula (I)

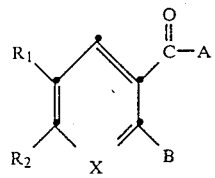

in which
X is a nitrogen atom,
and R$_2$ independently of one another are hydrogen or C$_1$–C$_4$alkyl,
A is —OH; —O$^\ominus$ M$^\oplus$; or C$_1$–C$_4$alkoxy,
M$^\oplus$ is the cation equivalent of an alkali metal or alkaline earth metal or of a nitrogen-containing base; and
B is a 2-imidazol-4-one radical of the formula

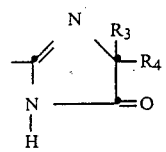

in which
R$_3$ is C$_1$–C$_4$alkyl and
R$_4$ is methyl or ethyl substituted by 1 to 5 fluorine atoms, or a salt thereof with an acid, base or complex-former.

2. A compound of formula I according to claim 1, in which R$^4$ is CHFCH$_3$, CHF$_2$ or CF$_3$.

3. 2-(5-methyl-5-trifluoromethylimidazol-4-on-2-yl)-isonicotinic acid,
2-(5-methyl-5-trifluoromethylimidazol-4-on-2-yl)-5-methylisonicotinic acid,
2-(5-methyl-5-trifluoromethylimidazol-4-on-2-yl)-5-ethylisonicotinic acid,
2-[5-(1-fluoroethyl)-5-methylimidazol-4-on-2-yl]-isonicotinic acid,
2-[5-(1-fluoroethyl)-5-methylimidazol-4-on-2-yl]-5-methylisonicotinic acid,
2-[5-(1-fluoroethyl)-5-methylimidazol-4-on-2-yl]-5-ethylisonicotinic acid,
2-[5-difluoromethyl-5-methylimidazol-4-on-2-yl]-isonicotinic acid,
2-[5-difluoromethyl-5-methylimidazol-4-on-2-yl]-5-methylisonicotinic acid,
2-[5-difluoromethyl-5-methylimidazol-4-on-2-yl]-5-ethylisonicotinic acid,
2-[5-(1-fluoroethyl)-5-methylimidazol-4-on-2-yl]-isonicotinic acid methyl ester,
2-[5-(1-fluoroethyl)-5-methylimidazol-4-on-2-yl]-isonicotinic acid ethyl ester or
2-[5-(1-fluoroethyl)-5-methylimidazol-4-on-2-yl]-5-ethylisonicotinic acid ethyl ester according to claim 1.

4. A herbicidal composition which comprises a herbicidally effective amount of a compound of formula I according to claim 1 together with an agriculturally acceptable carrier or adjuvant.

5. A method of controlling undesired plant growth, wherein a herbicidally effective amount of a compound of formula I according to claim 1 is allowed to act on the locus of the plant to be controlled.

6. A method according to claim 5 for the selective control of weeds in crops of useful plants.

7. A method according to claim 6 wherein the useful plants are cereals, cotton, soybean, maize, rice or sorghum plants.

* * * * *